United States Patent
Lu et al.

(10) Patent No.: US 11,827,940 B2
(45) Date of Patent: Nov. 28, 2023

(54) METHOD FOR DETECTING CANCER USING 5-HYDROXYMETHYLCYTOSINE (5-HMC)

(71) Applicants: Yabin Lu, Pleasanton, CA (US); Michael Jinyang Lu, Pleasanton, CA (US)

(72) Inventors: Yabin Lu, Pleasanton, CA (US); Michael Jinyang Lu, Pleasanton, CA (US)

( * ) Notice: Subject to any disclaimer, the term of this patent is extended or adjusted under 35 U.S.C. 154(b) by 0 days.

(21) Appl. No.: 17/961,571

(22) Filed: Oct. 7, 2022

(65) Prior Publication Data

US 2023/0227915 A1    Jul. 20, 2023

Related U.S. Application Data

(63) Continuation-in-part of application No. 17/577,033, filed on Jan. 17, 2022, now abandoned.

(51) Int. Cl.
*C12Q 1/6886*   (2018.01)
*C12Q 1/6806*   (2018.01)

(52) U.S. Cl.
CPC ......... *C12Q 1/6886* (2013.01); *C12Q 1/6806* (2013.01); *C12Q 2600/112* (2013.01); *C12Q 2600/156* (2013.01); *C12Q 2600/166* (2013.01)

(58) Field of Classification Search
CPC ............ C12Q 2600/166; C12Q 1/6886; C12Q 1/6806; C12Q 2600/112; C12Q 2600/156
See application file for complete search history.

(56) References Cited

U.S. PATENT DOCUMENTS

2021/0108274 A1 *  4/2021  Arensdorf ................ G16B 5/20

* cited by examiner

*Primary Examiner* — Cynthia B Wilder
(74) *Attorney, Agent, or Firm* — Ashok Tankha

(57) ABSTRACT

Disclosed herein is a method which includes extracting genomic deoxyribonucleic acid (DNA) at locations at or near cancer hotspots from a subject, modifying Tier-1 5hmC on the DNA to a modified 5hmC, detecting and identifying the presence or absence of the modified 5hmC, quantifying the detected and identified modified 5hmC; and providing a report comprising a score, wherein the score is indicative of the presence of cancer.

15 Claims, 10 Drawing Sheets

METHOD FOR DETECTING CANCER USING 5-HYDROXYMETHYLCYTOSINE (5-HMC)

CROSS REFERENCE TO RELATED APPLICATION

This application is a continuation-in-part of non-provisional patent application titled "Method For Detecting Cancer Using 5-Hydroxymethylcytosine (5-hmC)", application Ser. No. 17/577,033, filed in the United States Patent and Trademark Office on Jan. 17, 2022. The specification of the above referenced patent application is incorporated herein by reference in its entirety.

FIELD OF THE INVENTION

The present disclosure relates to a method for detecting cancer. More particularly, it relates to a method for detecting, screening or predicting a likelihood of cancer using specific genomic 5-hydroxymethylcytosine (5hmC) sites at or near cancer mutation hot spots.

BACKGROUND

Cancer is a major disease worldwide. Each year, tens of millions of people are diagnosed with cancer around the world, and more than half of the patients eventually die from it. In many countries, cancer ranks the second most common cause of death following cardiovascular diseases. Early detection of cancer in a person improves the cure and outcomes for many types of cancers.

Efforts in using mutation hotspots as cancer biomarkers have not been fully successful due to the fact that cancer is usually associated with many mutations. These hotspots often do not show up in the majority of cancer cases. No single hotspot is prevalent enough to be used as a universal sensitive cancer marker. Universal markers like methylated cytosine (5-methylcytosine or 5mC) and Tumor Mutation Burden (TMB) have been widely explored as simple markers. However, both markers still lack large-scale validation, precluding implementation in clinical practice.

Mammalian deoxyribonucleic acid (DNA) contains oxidized forms of 5-methylcytosine (5mC). The base 5-hydroxymethylcytosine (5hmC) is the most commonly occurring oxidation product. In one well known mechanism, 5hmC is produced from 5mC in an enzymatic pathway involving three 5mC oxidases, Ten-eleven translocation (TET)1, TET2, and TET3. Formation of 5hmC from 5mC lowers the levels of 5mC genome. The conversion of 5mC to 5hmC may be the first step in a pathway leading towards DNA demethylation. However, the biological role of 5hmC is still unclear, and there may be conflicting results on inhibition of TET and suppressed hydroxymethylation (5hmC), such as promoting somatic cell reprogramming, increased gene expression of tumor suppression, and reduced cholangiocarcinoma progression.

Studies on the functional role of 5hmC have been heavily focused on change in chromosome-wide global 5hmC density or concentration, or regulation of transcription in the promoter region, or loss of 5hmc across many types of cancer. Unlike the uniform distribution of 5mC outside of the promoter regions, satellites, and repeat DNA sequences, 5hmC has distinct distributions across different functional regions, and its abundance varies across different tissues and cell types. Tissue type plays a dominant role in determining the distribution patterns of 5hmC. 5hmC is enriched primarily in the distal regulatory regions, gene bodies of actively expressing genes and promoters, indicating its connection with active transcription. Genome-wide analysis of 5mC has indicated the global hypo-methylation pattern in tumor tissues, whereas depletion of 5hmC has also been associated with the hyper-methylation of gene bodies in various cancers. Significant enrichment of 5hmC is observed in both tissue-specific and cancer-specific differentially methylated regions as compared with that of 5mC.

Using massive parallel sequencing technique, thousands of genes from pancreatic cancer patients were simultaneously studied in which 5hmC is differentially expressed. Hundreds of genes related to pancreatic development or cancer were found to carry many 5hmC sites. By measuring signal ("peaks') from thousands of 5hmC all together, "global" 5hmC profiles or patterns in either increase or decrease were observed at chromosomal or at clusters of gene sequence level. For example, the size of the group was described as "log [counts per million (base pair)] on 320 genes, a subset of the 13,180 genes that exhibited a statistically significant (FDR=0.05) increase or decrease in 5hmC". Even though sample genes and their genomic locations are listed based on filtering criteria, each gene was covered by a few thousand base pair sequence, without pointing out which specific, individual 5hmC sites. However, there is no identification of specific individual 5hmC sites linked to cancer or hotspot mutations linked to cancer. But rather it was assumed the individual hydroxymethylation biomarkers may not have significant individual significance in the evaluation of a pancreatic lesion.

In our study, we demonstrated that, after chemical treatment to convert it to uracil (read as Thymine in NGS sequencing), 5hmCs are detected within CpG islands located either at or near a cancer mutation hotspot (within an 80 bp flanking region). 5hmC detected on these discrete CpG sites showed a significantly greater proportion of cancer versus normal cells. The results showed that the 5hmCs detected at or near caner mutation hotspots consist near entirely by two characteristically distinct 5hmC groups: Tier 1 Group: the cytosine (C) residues that exhibit 3 to 8-fold more likelihood of 5hmCs detected in gDNAs from tumor-cells than from normal-cells; Tier 2 group: equal allele frequency (AF) of 5hmc detected in both normal and tumor-cells. It was hypothesized that, the Tier 1 group of 5hmC is associated with cancer cells and cancer hotspot formation. The 5hmC is an intermediate or precursor before the eventual C to T or G to A mutation. Unlike previous studies looking at the "global" 5hmC signals or patterns of 5hmC (as a group) across large chromosomal region, this study is based on identified specific, individual 5hmC sites at or near known cancer hotspots that display higher 5hmC occurrence in cancer cells. Tier 1 sites individually or combinedly detected can serve as specific marker for cancer. In Tier 2 5hmC sites, both cancer and normal cells have similar level of 5hmC. Tier 2 sites are not good as marker to distinguish between cancer and normal cells.

The detection of these specifically selected, individual Tier-1 5hmC sites at or near hotspot CpG sites in cancer cell can be a more convenient, more direct, and more sensitive cancer detection method than analysing the methylation profile at chromosomal level or from hundreds of sequences of entire genes.

Thus, there is a need for methods for detecting cancer using these specifically located 5hmCs directly at specific base (C or G) resolution.

SUMMARY OF THE INVENTION

A method is disclosed to detect risk of cancer. The method includes extracting genomic deoxyribonucleic acid (DNA)

from locations at or near cancer hotspots from a subject, modifying the specific Tier-1 5-hydroxymethylcytosine (5hmC) on the DNA to a modified specific Tier-1 5hmC, detecting and identifying presence or absence of modified Tier-1 5hmC, quantifying the detected and identified modified specific Tier-1 5hmC, and providing a report comprising a score, wherein the score is indicative of the likelihood of a status, a degree, or a severity of the risk of cancer, wherein the specific Tier-1 exist in cancer cell lines, in transformed and immortalized cells.

DETAILED DESCRIPTION OF THE INVENTION

Figure 1A:
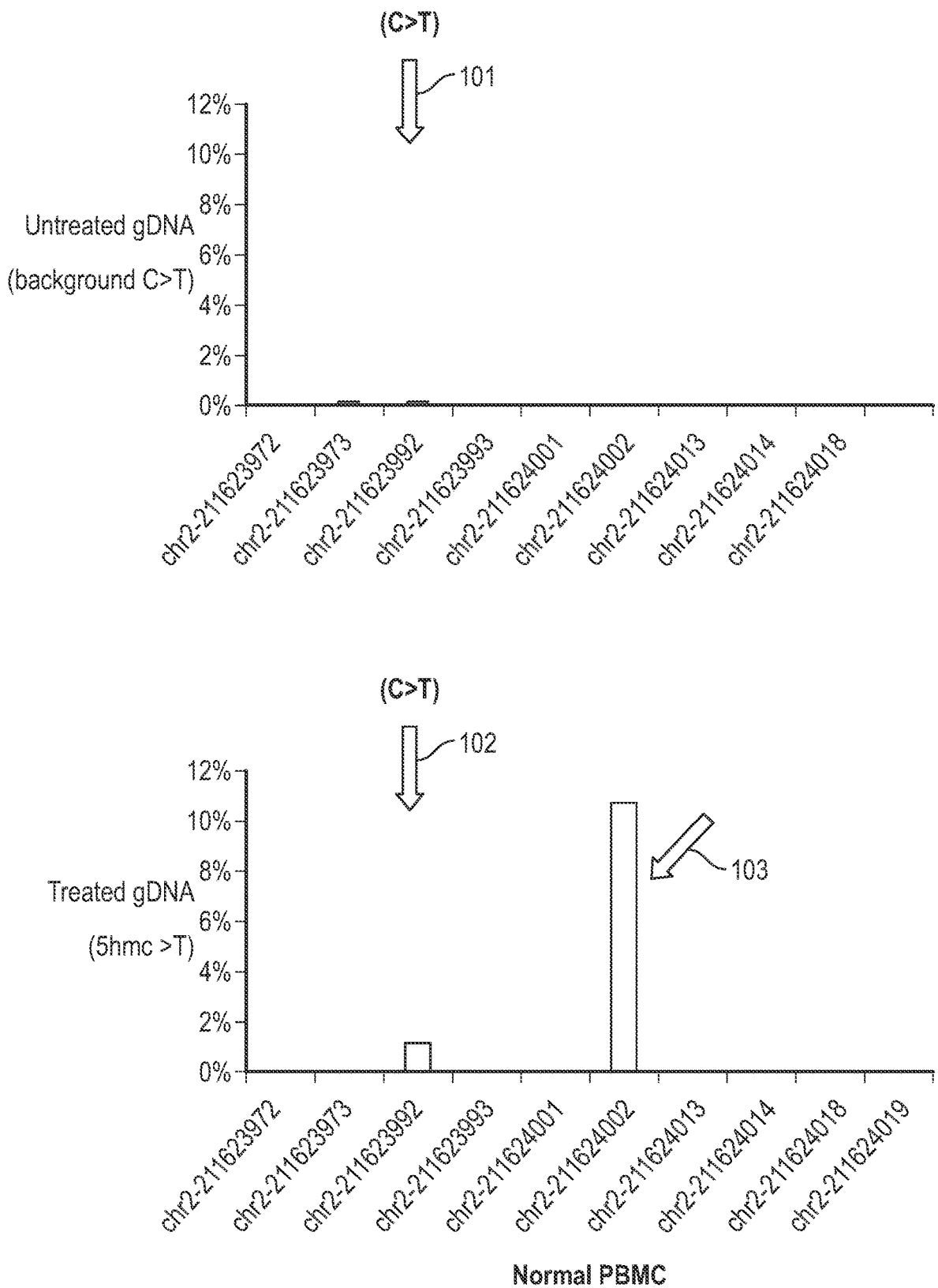
FIGS. 1A-1C and 2A-2D illustrate examples of individual 5hmC sites as specific cancer marker (Tier 1) or not as marker (Tier 2).

Before explaining at least one embodiment of the disclosure in detail, it is to be understood that the disclosure is not necessarily limited in its application to the details set forth in the following description. The disclosure is capable of other embodiments, and of being practiced or carried out in various ways. Also, it is to be understood that the phraseology and terminology employed herein is for the purpose of description and should not be regarded as limiting.

As used herein, a cancer mutation hot spot is any single nucleotide having C-to-T or G-to-A substitution mutations reported in the literature that is associated with any cancer. A C>T or G>A change at hotspot resulted in an amino acid change, such as ATM p.R337C, SMARCA4 p.T790M, IDH1 p.R137H, KRAS p.G12C, etc. By way of example, hotspots comprise the following (Table 1):

TABLE 1

| Gene | HGVS.p* | Chromosome | Position (start) | Position (end) | Substitutions† | Number of affected samples |
|---|---|---|---|---|---|---|
| AACS | p.P495H | chr12 | 125,129,395 | 125,129,395 | C > A | 1 |
| AADAT | p.L84F | chr4 | 170,087,233 | 170,087,233 | C > A | 1 |
| AAK1 | p.E341D | chr2 | 69,525,065 | 69,525,065 | C > A | 1 |
| AAMP | p.E57D | chr2 | 218,269,485 | 218,269,485 | C > A | 1 |
| ABCA10 | p.E1521D | chr17 | 69,148,896 | 69,148,896 | C > A | 1 |
| ABCA2 | p.K2310N | chr9 | 137,008,951 | 137,008,951 | C > A | 1 |
| ABCA2 | p.W750C | chr9 | 137,017,654 | 137,017,654 | C > A | 1 |
| ABCB1 | p.E686D | chr7 | 87,544,829 | 87,544,829 | C > A | 1 |
| ABCB6 | p.R177M | chr2 | 219,218,144 | 219,218,144 | C > A | 1 |
| ABCB8 | p.P68H | chr7 | 151,033,712 | 151,033,712 | C > A | 1 |
| ABCC10 | p.L657I | chr6 | 43,438,721 | 43,438,721 | C > A | 1 |
| ABCC10 | p.P724H | chr6 | 43,442,998 | 43,442,998 | C > A | 1 |
| ABCC3 | p.H93N | chr17 | 50,656,756 | 50,656,756 | C > A | 1 |
| ABCC3 | p.P1109Q | chr17 | 50,676,536 | 50,676,536 | C > A | 1 |
| ABCD4 | p.S307I | chr14 | 74,292,764 | 74,292,764 | C > A | 1 |
| ABHD13 | p.P32H | chr13 | 108,229,313 | 108,229,313 | C > A | 1 |
| ABHD15 | p.G69V | chr17 | 29,566,761 | 29,566,761 | C > A | 1 |
| ABU | p.R490L | chr10 | 26,748,628 | 26,748,628 | C > A | 1 |
| ABU | p.E424D | chr10 | 26,751,677 | 26,751,677 | C > A | 1 |
| AASDH | p.L440fs | chr4 | 56,354,102 | 56,354,102 | C > CA | 5 |
| ABLIM1 | p.C106fs | chr10 | 114,601,889 | 114,601,889 | C > CA | 1 |
| ACO2 | p.I742fs | chr22 | 41,528,493 | 41,528,493 | C > CA | 1 |
| ADD3 | p.W364fs | chr10 | 110,122,233 | 110,122,233 | C > CA | 1 |
| ADD3 | p.E670fs | chr10 | 110,133,591 | 110,133,591 | C > CA | 1 |
| AGGF1 | p.N681fs | chr5 | 77,063,141 | 77,063,141 | C > CA | 2 |
| AGL | p.N1304fs | chr1 | 99,912,471 | 99,912,471 | C > CA | 2 |
| AGTPBP1 | p.L1104fs | chr9 | 85,575,386 | 85,575,386 | C > CA | 1 |
| ANKRD12 | p.N1526fs | chr18 | 9,257,837 | 9,257,837 | C > CA | 1 |
| ANO10 | p.G229fs | chr3 | 43,577,169 | 43,577,169 | C > CA | 1 |
| AP4B1 | p.C320fs | chr1 | 113,900,059 | 113,900,059 | C > CA | 1 |
| APAF1 | p.N591fs | chr12 | 98,677,428 | 98,677,428 | C > CA | 4 |
| APC | p.K2051fs | chr5 | 112,841,737 | 112,841,737 | C > CA | 1 |
| ARCN1 | p.A180fs | chr11 | 118,583,892 | 118,583,892 | C > CA | 1 |
| ARF1 | p.E17fs | chr1 | 228,097,156 | 228,097,156 | C > CA | 1 |
| ARFGAP3 | p.A153fs | chr22 | 42,834,262 | 42,834,262 | C > CA | 1 |
| ARHGAP18 | p.L626fs | chr6 | 129,580,092 | 129,580,092 | C > CA | 1 |
| ARHGAP19 | p.V46fs | chr10 | 97,266,046 | 97,266,046 | C > CA | 1 |
| ARHGAP5 | p.P193fs | chr14 | 32,091,238 | 32,091,238 | C > CA | 1 |
| ARID1B | p.N1782fs | chr6 | 157,206,517 | 157,206,517 | C > CA | 1 |
| ARIH2 | p.H129fs | chr3 | 48,964,975 | 48,964,975 | C > CA | 1 |
| CEP162 | p.D407fs | chr6 | 84,186,514 | 84,186,514 | C > CAA | 1 |
| UBA52 | p.K114dup | chr19 | 18,575,096 | 18,575,096 | C > CAAG | 1 |
| ATP6V1C2 | p.S316fs | chr2 | 10,777,692 | 10,777,692 | C > CAG | 3 |
| DSP | p.E1778fs | chr6 | 7,581,510 | 7,581,510 | C > CAG | 1 |
| FIP1L1 | p.E488fs | chr4 | 53,453,080 | 53,453,080 | C > CAG | 4 |
| LMO7 | p.N937fs | chr13 | 75,841,170 | 75,841,170 | C > CAG | 1 |
| RB1 | p.A74fs | chr13 | 48,307,352 | 48,307,352 | C > CAG | 2 |
| APOBR | p.E183dup | chr16 | 28,495,573 | 28,495,573 | C > CAGG | 1 |

TABLE 1-continued

| Gene | HGVS.p* | Chromosome | Position (start) | Position (end) | Substitutions† | Number of affected samples |
|---|---|---|---|---|---|---|
| CCDC97 | p.E245dup | chr19 | 41,319,792 | 41,319,792 | C > CAGG | 1 |
| NHSL1 | p.P938dup | chr6 | 138,431,542 | 138,431,542 | C > CAGG | 1 |
| SERAC1 | p.V77fs | chr6 | 158,150,489 | 158,150,489 | C > CAT | 2 |
| H1FX | p.M1fs | chr3 | 129,315,900 | 129,315,900 | C > CATGGT | 1 |
| FGFRL1 | p.S486fs | chr4 | 1,025,266 | 1,025,266 | C > CCACA | 2 |
| EDC4 | p.S617dup | chr16 | 67,879,863 | 67,879,863 | C > CCAG | 2 |
| MED15 | p.Q218dup | chr22 | 20,564,628 | 20,564,628 | C > CCAG | 3 |
| RAI1 | p.Q291dup | chr17 | 17,793,779 | 17,793,779 | C > CCAG | 1 |
| ATN1 | p.Q488_Q489dup | chr12 | 6,936,716 | 6,936,716 | C > CCAGCAA | 1 |
| ATR | p.Y239_G240insVEY | chr3 | 142,562,683 | 142,562,683 | C > CCATACTCTA | 1 |
| DCTN1 | p.E218dup | chr2 | 74,371,166 | 74,371,166 | C > CCCT | 1 |
| BRD7 | p.D278fs | chr16 | 50,334,766 | 50,334,766 | C > CCT | 4 |
| KIAA0907 | p.D517fs | chr1 | 155,916,630 | 155,916,630 | C > CCT | 1 |
| RNF43 | p.E79dup | chr17 | 58,415,339 | 58,415,339 | C > CCTT | 1 |
| ASUN | p.R573Q | chr12 | 26,913,544 | 26,913,544 | C > T | 1 |
| ASXL1 | p.A221V | chr20 | 32,429,997 | 32,429,997 | C > T | 1 |
| ASXL1 | p.R417X | chr20 | 32,433,447 | 32,433,447 | C > T | 1 |
| ASXL1 | p.R1415X | chr20 | 32,436,955 | 32,436,955 | C > T | 1 |
| ASXL2 | p.G79R | chr2 | 25,806,246 | 25,806,246 | C > T | 1 |
| ATAD1 | p.R201H | chr10 | 87,776,409 | 87,776,409 | C > T | 1 |
| ATAD2 | p.C387Y | chr8 | 123,359,683 | 123,359,683 | C > T | 1 |
| ATAD2 | p.R313H | chr8 | 123,369,169 | 123,369,169 | C > T | 1 |
| ATAD2B | p.R514H | chr2 | 23,857,442 | 23,857,442 | C > T | 1 |
| ATAD5 | p.S634L | chr17 | 30,835,982 | 30,835,982 | C > T | 1 |
| ATAD5 | p.P1630L | chr17 | 30,893,742 | 30,893,742 | C > T | 1 |
| ATE1 | p.A502T | chr10 | 121,743,733 | 121,743,733 | C > T | 1 |
| ATE1 | p.G236S | chr10 | 121,902,498 | 121,902,498 | C > T | 1 |
| ATF2 | p.R342H | chr2 | 175,093,221 | 175,093,221 | C > T | 1 |
| ATF4 | p.A98V | chr22 | 39,521,839 | 39,521,839 | C > T | 1 |
| ATF5 | p.R226C | chr19 | 49,932,919 | 49,932,919 | C > T | 1 |
| ATF6 | p.R376X | chr1 | 161,821,100 | 161,821,100 | C > T | 2 |
| ATF6B | p.V168I | chr6 | 32,121,325 | 32,121,325 | C > T | 1 |
| ATF7 | p.R152H | chr12 | 53,534,607 | 53,534,607 | C > T | 1 |
| ATF7IP | p.P209L | chr12 | 14,424,541 | 14,424,541 | C > T | 1 |
| ATF7IP | p.A347V | chr12 | 14,424,955 | 14,424,955 | C > T | 1 |
| A1CF | p.R125C | chr10 | 50,836,305 | 50,836,305 | G > A | 1 |
| A1CF | p.R21C | chr10 | 50,859,880 | 50,859,880 | G > A | 1 |
| A2ME1 | p.A759T | chr12 | 8,851,824 | 8,851,824 | G > A | 1 |
| A4GALT | p.R213C | chr22 | 42,693,315 | 42,693,315 | G > A | 1 |
| AACS | p.R107Q | chr12 | 125,076,573 | 125,076,573 | G > A | 1 |
| AACS | p.G542D | chr12 | 125,134,799 | 125,134,799 | G > A | 1 |
| AACS | p.E580K | chr12 | 125,136,721 | 125,136,721 | G > A | 1 |
| AAK1 | p.T241M | chr2 | 69,530,641 | 69,530,641 | G > A | 1 |
| AAMDC | p.R69Q | chr11 | 77,869,795 | 77,869,795 | G > A | 1 |
| AAR2 | p.R207H | chr20 | 36,240,488 | 36,240,488 | G > A | 1 |
| AARS2 | p.A933V | chr6 | 44,300,707 | 44,300,707 | G > A | 1 |
| AARS2 | p.R521X | chr6 | 44,305,072 | 44,305,072 | G > A | 2 |
| AARS2 | p.A15V | chr6 | 44,313,280 | 44,313,280 | G > A | 1 |
| AARSD1 | p.R171X | chr17 | 42,956,439 | 42,956,439 | G > A | 1 |
| AASS | p.R910X | chr7 | 122,076,542 | 122,076,542 | G > A | 1 |
| AATF | p.R474Q | chr17 | 37,019,027 | 37,019,027 | G > A | 1 |
| AATK | p.R1124C | chr17 | 81,120,257 | 81,120,257 | G > A | 1 |
| AATK | p.A1101V | chr17 | 81,120,325 | 81,120,325 | G > A | 2 |
| AATK | p.A408V | chr17 | 81,122,404 | 81,122,404 | G > A | 1 |
| ABAT | p.A246T | chr16 | 8,768,893 | 8,768,893 | G > A | 1 |
| ABCAI | p.R1839C | chr9 | 104,793,292 | 104,793,292 | G > A | 1 |
| CCDC175 | p.N632fs | chr14 | 59,525,381 | 59,525,381 | G > GTT | 1 |
| AAAS | p.L128M | chr12 | 53,315,352 | 53,315,352 | G > T | 1 |
| AAGAB | p.H204N | chr15 | 67,209,470 | 67,209,470 | G > T | 1 |
| AAKI | p.P358H | chr2 | 69,520,971 | 69,520,971 | G > T | 1 |
| AASDHPPT | p.E299X | chr11 | 106,096,872 | 106,096,872 | G > T | 1 |
| ABCA2 | p.P1893Q | chr9 | 137,011,528 | 137,011,528 | G > T | 1 |
| ABCA5 | p.S1190Y | chr17 | 69,260,408 | 69,260,408 | G > T | 1 |
| ABCA7 | p.R1128M | chr19 | 1,053,491 | 1,053,491 | G > T | 1 |
| ABCA7 | p.G1374C | chr19 | 1,055,266 | 1,055,266 | G > T | 1 |
| ABCB10 | p.A647D | chr1 | 229,521,602 | 229,521,602 | G > T | 1 |
| ABCF3 | p.R546L | chr3 | 184,192,668 | 184,192,668 | G > T | 1 |
| ABHD14B | p.L69M | chr3 | 51,971,466 | 51,971,466 | G > T | 1 |
| ABI2 | p.K428N | chr2 | 203,427,208 | 203,427,208 | G > T | 1 |
| ABU | p.R1130M | chr9 | 130,885,679 | 130,885,679 | G > T | 1 |
| ABL1M3 | p.E247D | chr5 | 149,217,030 | 149,217,030 | G > T | 1 |

TABLE 1-continued

| Gene | HGVS.p* | Chromosome | Position (start) | Position (end) | Substitutions† | Number of affected samples |
|---|---|---|---|---|---|---|
| ACAD8 | p.K345N | chr11 | 134,261,833 | 134,261,833 | G > T | 1 |
| ACAP3 | p.A565D | chr1 | 1,295,747 | 1,295,747 | G > T | 1 |
| ACAT1 | p.R21M | chr11 | 108,121,668 | 108,121,668 | G > T | 1 |
| ACBD4 | p.G106C | chr17 | 45,137,040 | 45,137,040 | G > T | 1 |
| ACIN1 | p.L141M | chr14 | 23,090,591 | 23,090,591 | G > T | 1 |
| ACOT1 | p.K349N | chr14 | 73,543,436 | 73,543,436 | G > T | 1 |
| SNCAIP | p.E384fs | chr5 | 122,425,498 | 122,425,500 | TGA > T | 1 |
| TRIP11 | p.S1662fs | chr14 | 91,995,420 | 91,995,422 | TGA > T | 1 |
| UBAP2 | p.S699fs | chr9 | 33,933,499 | 33,933,501 | TGA > T | 1 |
| ZNF263 | p.R544fs | chr16 | 3,290,126 | 3,290,128 | TGA > T | 1 |
| AFAP1L1 | p.K694del | chr5 | 149,332,797 | 149,332,800 | TGAA > T | 1 |
| AKAP8 | p.F473del | chr19 | 15,360,955 | 15,360,958 | TGAA > T | 1 |
| BCR | p.K817del | chr22 | 23,287,193 | 23,287,196 | TGAA > T | 1 |
| CEP250 | p.K1467del | chr20 | 35,502,763 | 35,502,766 | TGAA > T | 1 |
| CIC | p.K1340del | chr19 | 42,293,809 | 42,293,812 | TGAA > T | 1 |
| FAM102B | p.K6del | chr1 | 108,560,433 | 108,560,436 | TGAA > T | 4 |
| GPATCH11 | p.E222del | chr2 | 37,094,135 | 37,094,138 | TGAA > T | 1 |
| GSPT2 | p.E502del | chrX | 51,745,120 | 51,745,123 | TGAA > T | 1 |
| KAT6B | p.E1073del | chr10 | 75,022,066 | 75,022,069 | TGAA > T | 2 |
| NAPA | p.F207del | chr19 | 47,492,059 | 47,492,062 | TGAA > T | 1 |
| PAF1 | p.F313del | chr19 | 39,388,385 | 39,388,388 | TGAA > T | 1 |
| PAIP2 | p.E42del | chr5 | 139,363,901 | 139,363,904 | TGAA > T | 1 |
| PHB2 | p.F52del | chr12 | 6,970,251 | 6,970,254 | TGAA > T | 1 |
| PLK1 | p.S471del | chr16 | 23,689,385 | 23,689,388 | TGAA > T | 1 |
| POLR3GL | p.E187del | chr1 | 145,978,078 | 145,978,081 | TGAA > T | 1 |
| RANBP2 | p.E2903del | chr2 | 108,781,372 | 108,781,375 | TGAA > T | 1 |
| RBM33 | p.E210del | chr7 | 155,700,823 | 155,700,826 | TGAA > T | 2 |
| SYBU | p.S174del | chr8 | 109,586,065 | 109,586,068 | TGAA > T | 3 |
| USP37 | p.S904del | chr2 | 218,457,093 | 218,457,096 | TGAA > T | 1 |
| SH3GLB2 | p.V257del | chr9 | 129,009,838 | 129,009,841 | TGAC > T | 1 |
| UBE3C | p.D1062del | chr7 | 157,267,686 | 157,267,689 | TGAC > T | 1 |
| URU | p.D311del | chr19 | 30,009,236 | 30,009,239 | TGAC > T | 5 |
| SNRNP70 | p.D375_R376del | chr19 | 49,108,251 | 49,108,257 | TGACCGC > T | 1 |
| AKAP13 | p.E363del | chr15 | 85,579,148 | 85,579,151 | TGAG > T | 1 |
| ATN1 | p.E75del | chr12 | 6,934,518 | 6,934,521 | TGAG > T | 1 |
| CREB3L4 | p.E193del | chr1 | 153,972,773 | 153,972,776 | TGAG > T | 1 |
| FMNL2 | p.R1071del | chr2 | 152,647,832 | 152,647,835 | TGAG > T | 2 |
| GTPBP2 | p.L385del | chr6 | 43,624,013 | 43,624,016 | TGAG > T | 1 |
| LIPH | p.S60del | chr3 | 185,535,002 | 185,535,005 | TGAG > T | 1 |
| NAB2 | p.E79del | chr12 | 57,091,269 | 57,091,272 | TGAG > T | 1 |
| NUDT17 | p.E132del | chr1 | 145,846,449 | 145,846,452 | TGAG > T | 1 |
| SRCAP | p.E2294del | chr16 | 30,736,346 | 30,736,349 | TGAG > T | 1 |
| UACA | p.L729del | chr15 | 70,668,496 | 70,668,499 | TGAG > T | 1 |
| ZFYVE26 | p.L2445del | chr14 | 67,752,379 | 67,752,382 | TGAG > T | 1 |
| CCAR1 | p.R324fs | chr10 | 68,749,527 | 68,749,531 | TGAGA > T | 1 |
| KAT6B | p.E1355_E1356del | chr10 | 75,028,874 | 75,028,880 | TGAGGAA > T | 1 |
| OSBPL11 | p.L302_S303del | chr3 | 125,563,803 | 125,563,809 | TGATAAA > T | 1 |
| URI1 | p.D307_D308del | chr19 | 30,009,233 | 30,009,239 | TGATGAC > T | 6 |
| HOXA3 | p.R195fs | chr7 | 27,108,661 | 27,108,663 | TGC > T | 1 |
| UTRN | p.K1448fs | chr6 | 144,491,004 | 144,491,008 | TGCAA > T | 1 |
| CCDC102A | p.R394del | chr16 | 57,518,132 | 57,518,135 | TGCC > T | 1 |
| PDX1 | p.P243del | chr13 | 27,924,562 | 27,924,565 | TGCC > T | 2 |
| HNRNPDL | p.P34_R36del | chr4 | 82,429,581 | 82,429,590 | TGCCGCGGCG > T | 1 |
| NCL | p.F690_G693del | chr2 | 231,455,244 | 231,455,256 | TGCCTCCTCGGAA > T | 1 |
| KEHE21 | p.A214fs | chr1 | 6,602,171 | 6,602,176 | TGCGCG > T | 1 |
| HEXIM1 | p.R323_E324del | chr17 | 45,150,155 | 45,150,161 | TGCGGGA > T | 2 |
| SH3D19 | p.A93fs | chr4 | 151,175,078 | 151,175,085 | TGCTTCCC > T | 1 |

*HGVS, human genome variation society;
†Reference sequence > Altered sequence

More examples include, but are not limited to, the hotspots identified in the following:

*Cancer Discov.* 2018 February; 8(2): 174-183 (Supplementary Material—Refer to Web version on PubMed Central for supplementary material); *Database: The Journal of Biological Databases and Curation*, 2020, 1-8; *npj Genomic Medicine* (2021) 6, Article number: 33; *Computational and Structural Biotechnology Journal*, Volume 18, 2020, Pages 3567-3576.

As used herein, the nearby region of the hotspot includes DNA with sequence 40 base pair upstream and 40 base pair downstream of the hotspot.

As used herein, Tier 1 5hmC are cytosine (C) residues that exhibit 3 to 8-fold more likelihood of becoming 5hmCs in genomic DNAs from tumor-cells than from normal-cells, and Tier 2 5hmC are sites that exhibit equal allele frequency of 5hmC in both normal and tumor-cells.

As used herein, the genomic DNA includes total or partial full-length or fragmented (i.e., cell-free DNA) genomic DNA isolated from any human tissues, including plasma.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes a human genome.

The term "subject" and "patient" are used interchangeably herein, and refer to an animal, for example, a human from whom cells can be obtained. The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

The term "sample" as used herein relates to a material or mixture of materials, typically, although not necessarily, in liquid form, containing one or more analytes of interest. Nucleic acid samples may be complex in that they contain multiple different molecules that contain sequences. Genomic DNA from a mammal (e.g., mouse or human) are types of complex samples. Any sample containing nucleic acid, e.g., genomic DNA made from tissue culture cells or a sample of tissue, may be employed herein.

Using chemical oxidation and reduction technique combined with Next Generation Sequencing (NGS), the present inventors explored the existence of 5hmC at cytosine and 5'-C-phosphate-G-3' (CpG) sites within the gene bodies of a group of oncogenes, especially at or near (e.g., within 40 base pairs) the known cancer mutation hotspots. The cancer mutation hotspot can be expressed as a single base on genomic DNA that is frequently observed to have single nucleotide variant (SNV). The present inventors found that 5hmC does not randomly exist on all CpG sites on a gene, but rather on a small portion of all the CpG sites or cytosine residues. They exist specifically at cytosine sites (mostly at cytosine in CpG islands) located right at or within a range of 40 base pairs of a cancer mutation hotspot. Sometimes 5hmC occurs on a cytosine (C) that is not adjacent to a guanine (G). The results show the presence of two characteristically distinct 5hmC groups: Tier 1 Group with 3 to 8-fold more 5hmCs detected in tumor-cells than in normal-cell derived DNA. Tier 2 group with equal allele frequency of 5hmc among normal and tumor-cell derived DNA at 5 CpG hotspot sites as well as 5 non-CpG hotspots. Significantly more Tier 1 group 5hmC sites are found at hotspots in either tumor cells or cell lines rendered immortal (by transforming agents such as SV40 T-antigen (Simian Vacuolating Virus 40 TAg)) than in healthy normal cells.

FIGS. 1A-1C and 2A-2D illustrates examples of individual 5hmc sites as specific cancer marker (Tier 1) or not as marker (Tier 2) i.e., Tier 1 and Tier 2 Group 5hmCs at or near hotspots.

Figure 1B:
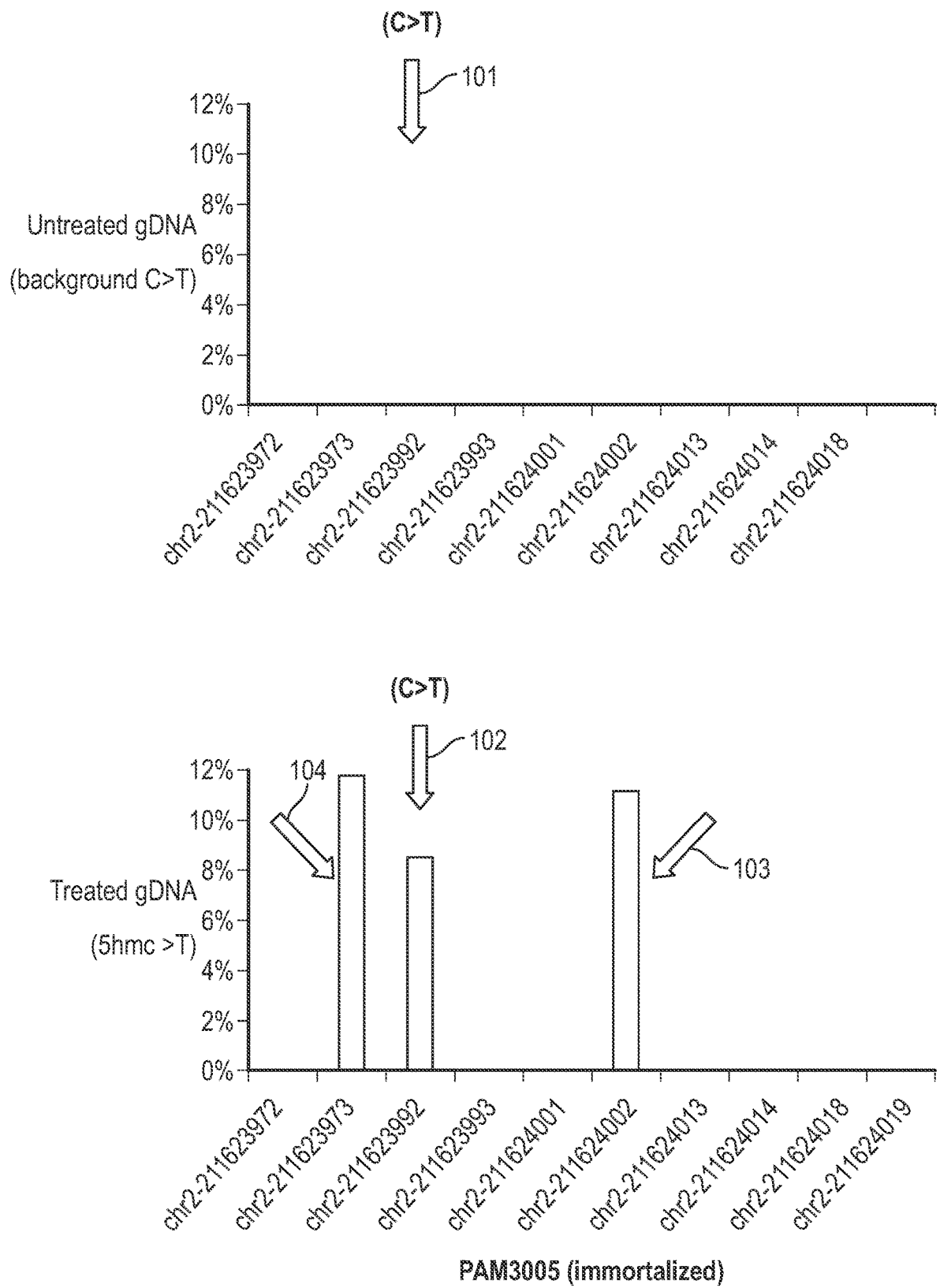
Figure 1C:
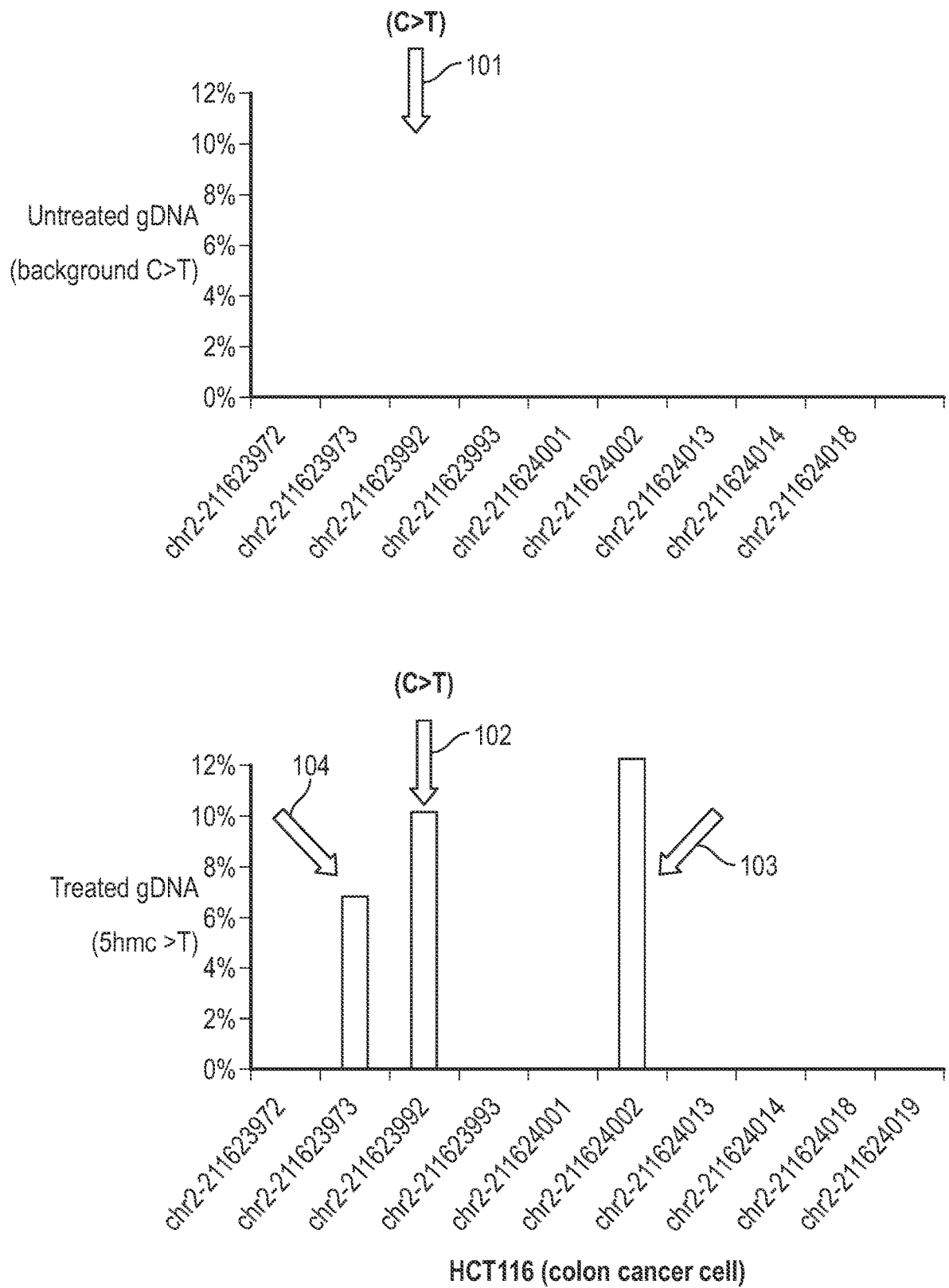
Figure 2A:
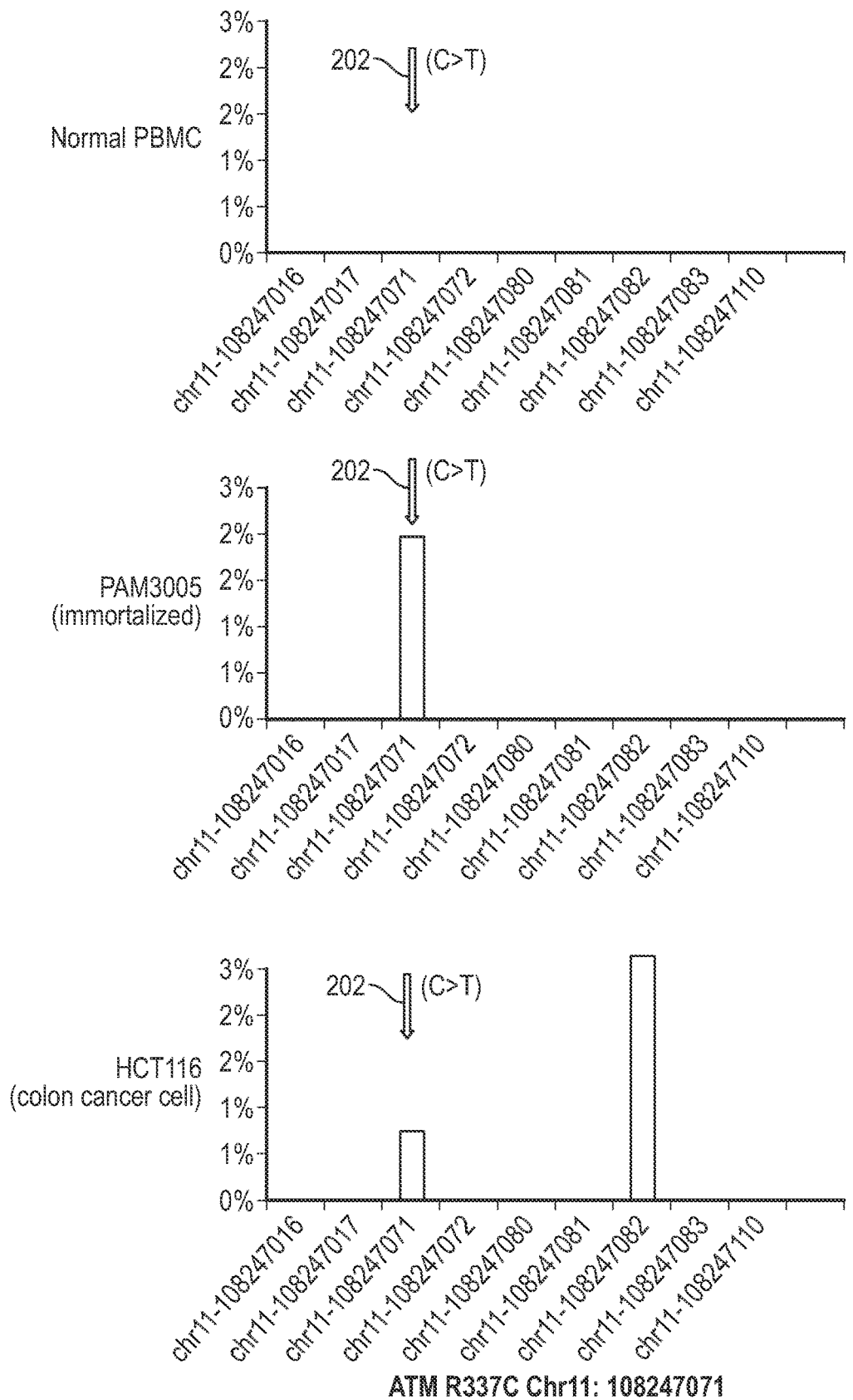
Figure 2B:
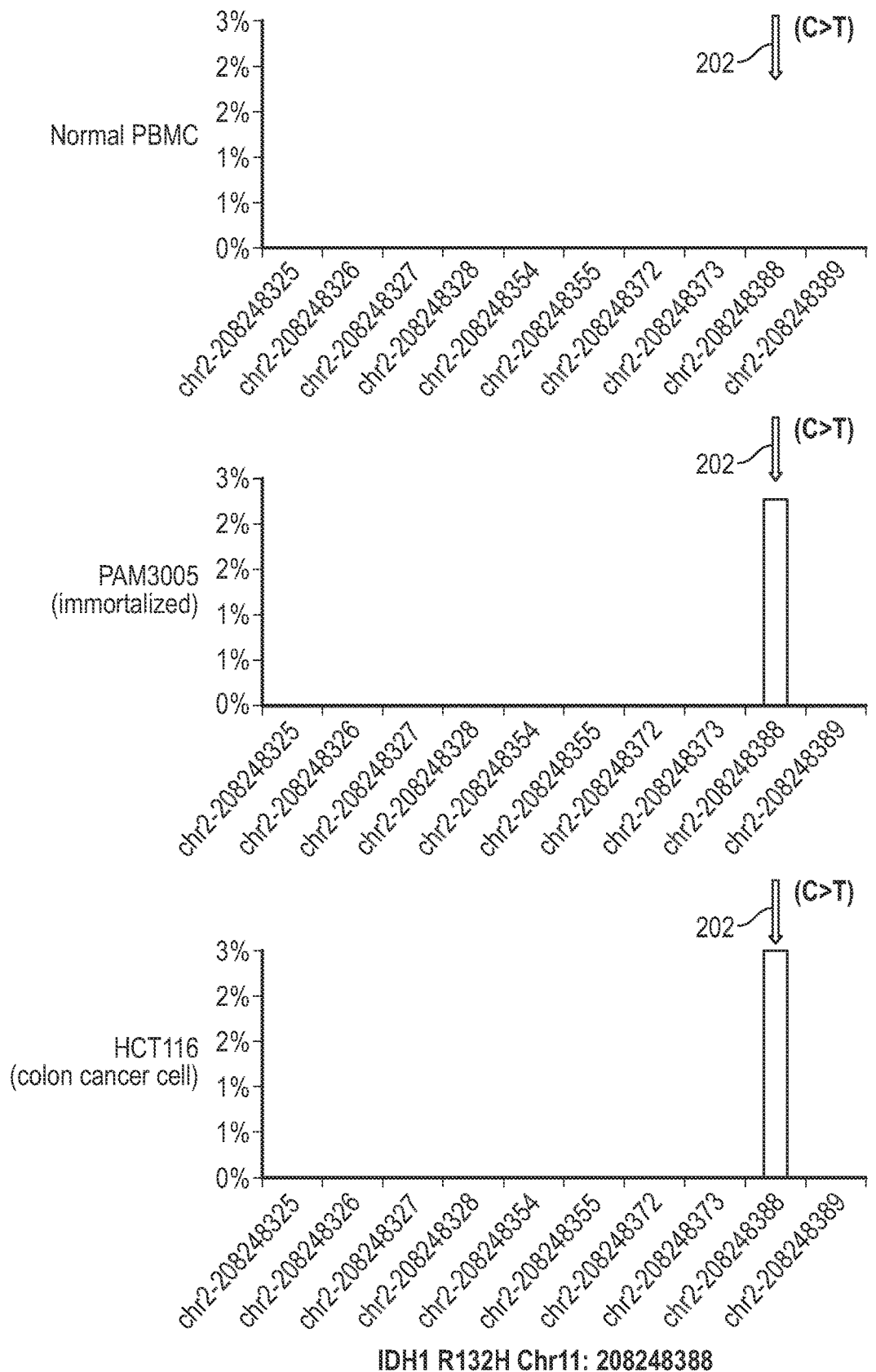
Figure 2C:
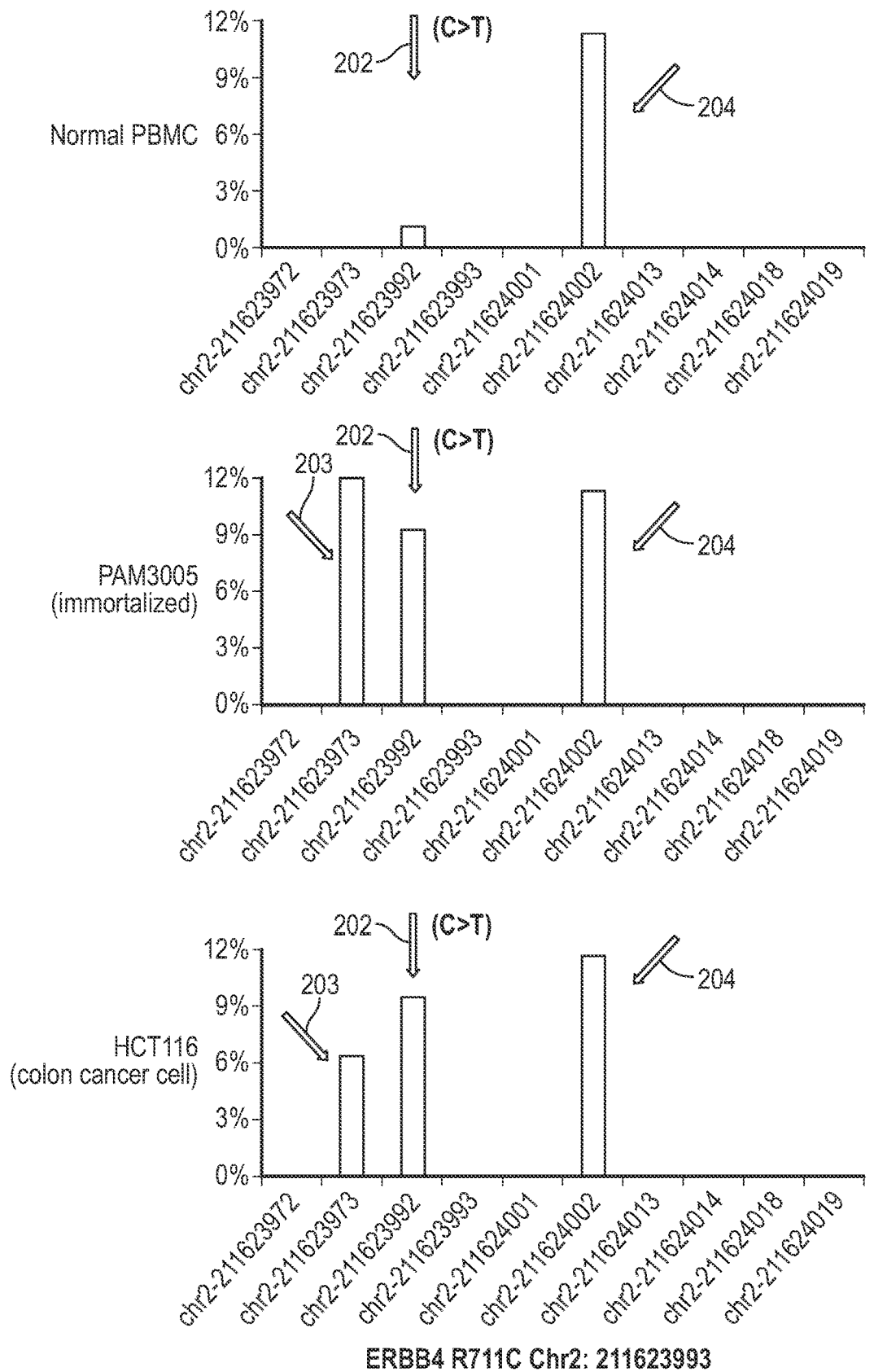
Figure 2D:
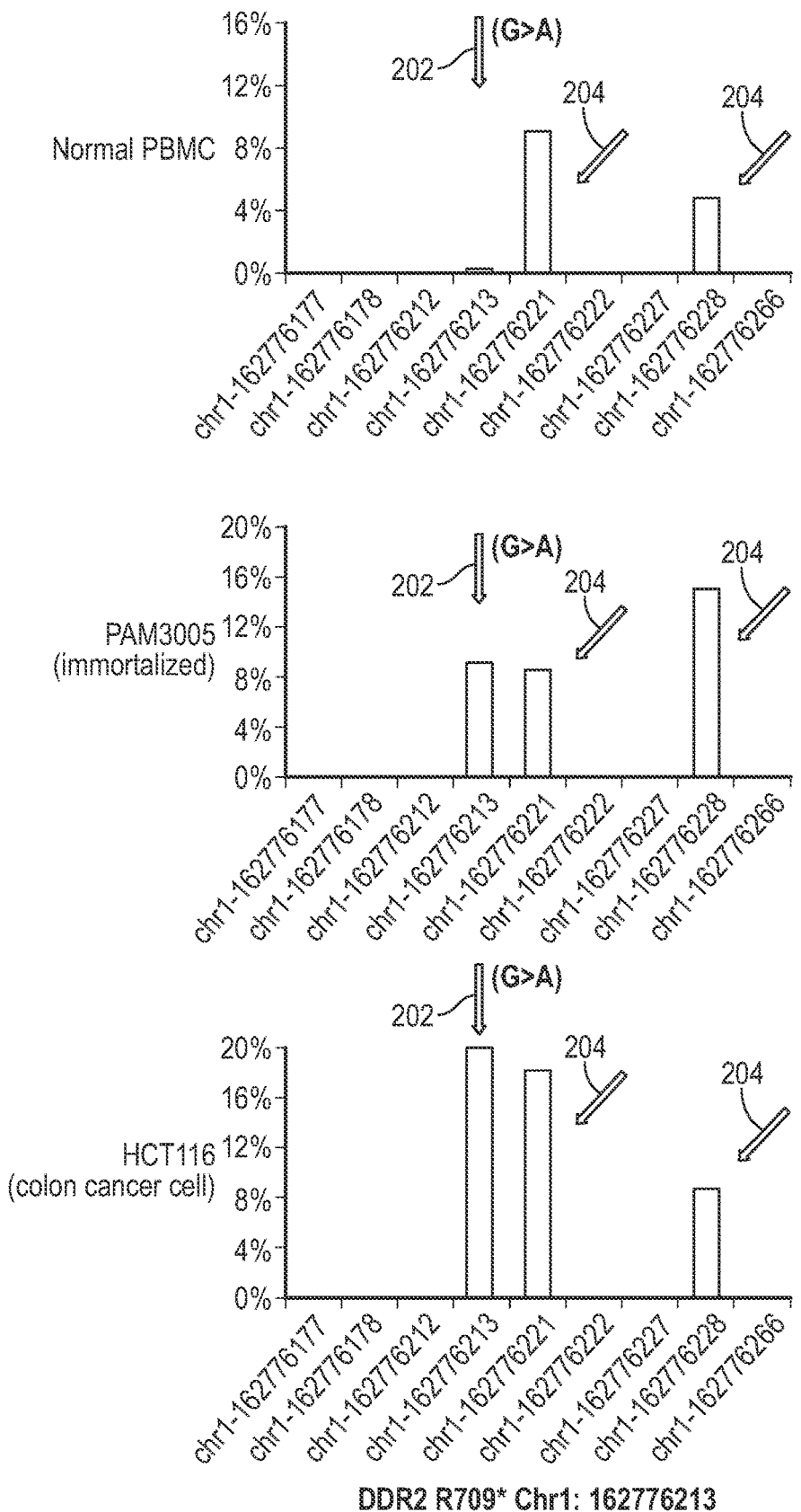

In particular, FIGS. 1A-1C are a representative Tier 1 observation (arrow 102) at cancer mutation hotspot ERBB4 R711C (Chr2: 211623993).

In FIGS. 1A-1C, the top half of the plots are for untreated, background level of hot spot mutation. The bottom half shows the treated group. Y-Axis: Allele Frequency (AF) shown as fraction of C>T mutation at all observed hotspots. X-Axis: genome coordinates of all nearby CpG sites. Vertical Arrows: Hotspot Location (Vertical arrows 101: Wild-type C or G; Vertical arrows 102: Mutation T or A); Arrows 103 (Tier 2 site): 5hmc detected in DNA from all cells; and Arrows 104 (Tier 1 site near hotspot): 5hmC detected in cancerous cells at non-hotspot CpG sites.

FIGS. 2A-2D illustrate several more examples of Tier 1 group. In FIGS. 2A-2D, Arrows 202 identify location of Tier 1 5hmc: at or near cancer mutation hotspots; Y-Axis: Allele Frequency (AF) shown as fraction of C>T mutation at all observed hotspots; X-Axis: genome coordinates of nearby CpG sites; Arrows 203 identify location of Tier 1 5mhc not at hotspot; and Arrows 204 identify location of Tier 2 5hmc detected in DNA from all cells.

Allele frequencies (AF %) of detected 5hmC at each cancer mutation hotspot (17 Hotspots) after the treatment are shown in Table 2 and Table 3. Examples of Tier 1 group 5hmC at cancer mutation hotspots (>8% are in bold) are listed in Table 2. Examples of Tier 2 group 5hmC at cancer mutation hotspots (>8% are in bold) are listed in Table 2.

TABLE 2

| Chromosome | Tier 1 Hotspot Location | Mutation name | Hotspot Mutation | Bases at hotspot | C of CpG Normal (PBMC) | G of CpG Normal (PBMC) | C of CpG Immprtalized (PAM3005) | G of CpG Immprtalized (PAM3005) | C of CpG Cancer (HCT116) | G of CpG Cancer (HCT116) |
|---|---|---|---|---|---|---|---|---|---|---|
| chr11 | 108247071 | ATMR337C, c.1009C > T | C > T | CpG | | | 2.1% | 56.8% | 0.7% | 8.1% |
| chr19 | 11021837 | SMARCA4T910M, c.2729C > T | C > T | CpG | | 2.0% | 6.1% | 1.1% | 2.2% | 10.7% |
| chr2 | 208248388 | IDH1R132H, c.395G > A | C > T | CpG | | 1.4% | 2.0% | 9.1% | 2.8% | 0.5% |
| chr1 | 162776212 | DDR2R709, c.2125C > T | C > T | CpG | 7.1% | 0.3% | 8.9% | 9.6% | 7.4% | 20.5% |
| chr17 | 39711955 | ERBB2S310F, c.929C > T | C > T | CpG | 3.8% | | 12.5% | | 16.6% | |
| chr2 | 211623993 | ERBB4R711C, c.2131C > T | G > A | CpG | 1.3% | 2.1% | 8.5% | 25.3% | 9.9% | 7.8% |
| chr12 | 25245350 | KRASG12C, c.34G > T | C > A | CC | | | 22.58% | | 32.14% | |

TABLE 3

| Chromosome | Tier 2 Hotspot Location | Mutation name | Hotspot Mutation | Bases at hotspot | C of CpG Normal (PBMC) | G of CpG Normal (PBMC) | C of CpG Immprtalized (PAM3005) | G of CpG Immprtalized (PAM3005) | C of CpG Cancer (HCT116) | G of CpG Cancer (HCT116) |
|---|---|---|---|---|---|---|---|---|---|---|
| chr17 | 7673802 | TP53R273H, c.818G > A | C > T | CpG | 1.2% | 4.1% | 2.5% | 4.8% | 5.0% | 3.3% |
| chr17 | 7674220 | TP53R248Q, c.743G > A | C > T | CpG | 5.8% | 0.6% | 8.7% | 0.4% | 5.5% | 2.4% |
| chr7 | 55181378 | EGFRT790M, c.2369C > T | C > T | CpG | 7.4% | 4.8% | 6.4% | | 6.0% | 0.7% |
| chr17 | 7675088 | TP53R175H, c.524G > A | C > T | CpG | 2.3% | 4.8% | 0.8% | 6.3% | 3.4% | 6.6% |
| chr5 | 112839941 | APCR1450, c.4348C > T | G > A | CpG | | 6.3% | | 6.7% | | 18.6% |
| chr15 | 66436824 | MAP2K1P124S, c.370C > T | C > T | CC | 7.2% | | 5.7% | | 3.8% | |
| chr14 | 104780214 | AKT1E17K, c.49G > A | C > T | CC | 2.8% | | 1.9% | | 4.7% | |
| chr3 | 41224646 | CTNNB1S45F, c.134C > T | C > T | TCT | 2.1% | | 1.5% | | 1.0% | |
| chr3 | 179218303 | PIK3CAE545K, c.1633G > A | G > A | TGA | | 2.6% | | 4.2% | | 5.4% |
| chrX | 71119404 | MED12G44D, c.131G > A | G > A | GG | | 5.1% | | 5.4% | | 5.9% |

DNAs from normal cells (PBMC) and the two cancerous/tumor cells are compared. Both base C and G of the CpG are checked. AFs higher than 8% are shown in bold and those between 4% and 8% can also be noted. In cancerous cells, most CpG hotspot sites have both the C and G in the CpG island mutated. One of the non-CpG hotspot, KRAS G12C (a "CC", with a C to A mutation), showed significantly more 5hmCs in cancerous cells than in normal cells.

Figure 3:
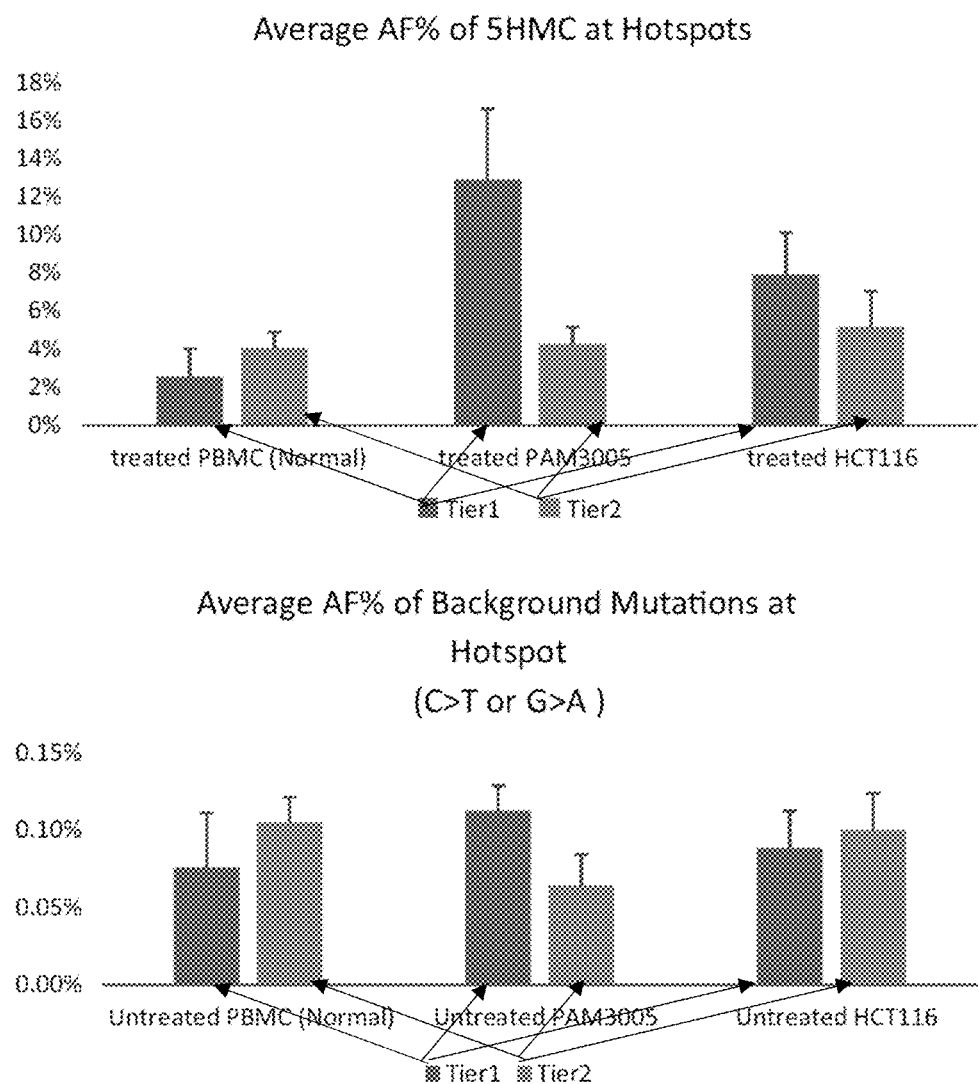
FIG. 3 illustrates average AF % of detected C>T (G>A) at hotspots before and after DNA treatment.

The observations in Table 1 and 2, averaged AF % for each group, before or after the 5hmC>T conversion are plotted in FIG. 3. Significantly higher AF % are observed in both PAM3005 (transformed cells) and HCT116 (cancer cell lines) in Tier 1, while the AF % were comparable among Tier 2. Background level of AF % for all groups are comparable.

In an expanded studies covering 33 cancer mutation hotspots employing 12 normal and 12 colorectal cancer samples further confirmed the above results in cell culture cells. Significantly more 5hmC sites were observed in tumor than normal DNA at higher AF. For example, at 5% AF or above, an average of 609 5hmC sites were found in each tumor DNA versus 479 in normal DNA. At 10% or higher, the average number was about 153 in tumor versus 66 in normal. The number of extra 5hmC (Tier 1) found in tumor was proportionally higher in high AF range. Calculated as percentage of 5hmC sites found in normal, there were 2%, 36%, 170%, and 283% more 5hmC counts in tumor, and 24%, 46%, 147% and 230% higher sum of AF values in tumor than in normal gDNA, when detection criteria of AF were set at above 1%, 5%, 10 and 12%, respectively (See, FIG. 4).

Figure 4:
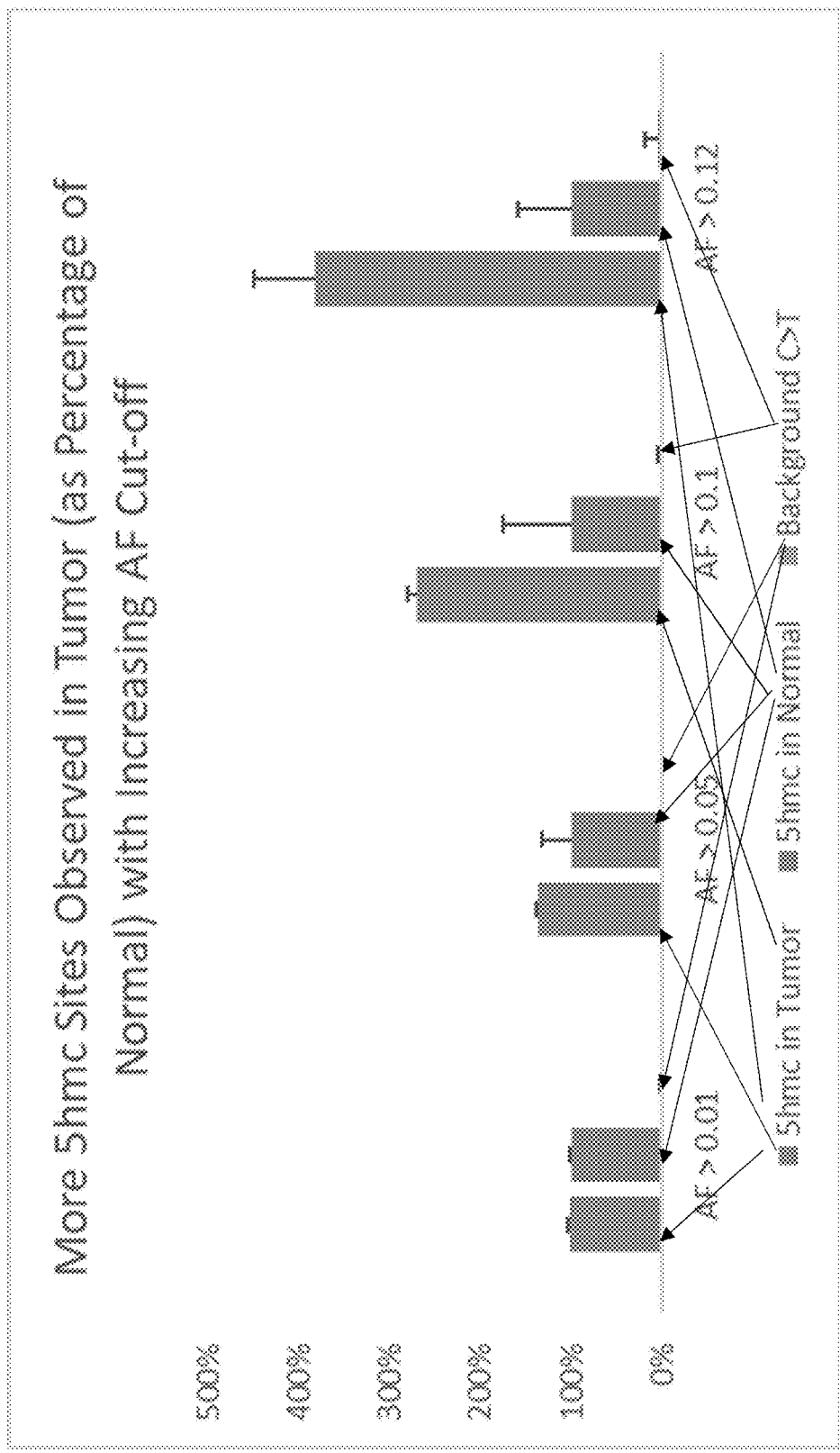
FIG. 4 illustrates 5hmC sites in tumor as percentage of 5hmC in normal at increasing AF cut-off.

FIG. 4. Illustrates 5hmC sites in tumor as percentage of 5hmC in normal at increasing AF cut-off.

Tier 1 5hmC sites showing three-fold or higher AF in colorectal tumor cells than in normal colon cells (in the 80 bp hotspot flanking regions studied) are listed in Table 4 (Cancer Hotspot Targets with Single Nucleotide Variant (SNV) below. About half of these sites coincide with known mutation hotspots. Table 4 does not include all Tier 1 sites that are not detected in the experiment nor all Tier 1 sites in cells from other tumor types.

TABLE 4

| Chromosome | Genomic Location (Hg38) | Base | Gene |
|---|---|---|---|
| chr1 | 114713883 | G | NRAS |
| chr1 | 114713893 | G | NRAS |
| chr1 | 114713898 | G | NRAS |
| chr1 | 114713917 | G | NRAS |
| chr1 | 114713930 | C | NRAS |
| chr1 | 114713945 | C | NRAS |
| chr1 | 162776178 | C | DDR2 |
| chr1 | 204537412 | G | MDM4 |
| chr1 | 204537448 | C | MDM4 |
| chr1 | 204537462 | C | MDM4 |
| chr2 | 211623981 | C | ERBB4 |
| chr3 | 179234268 | G | PIK3CA |
| chr3 | 41224650 | G | CTNNB1 |
| chr3 | 41224652 | G | CTNNB1 |
| chr4 | 1801808 | G | FGFR3 |
| chr4 | 1801845 | G | FGFR3 |
| chr4 | 1801863 | G | FGFR3 |
| chr4 | 54285923 | G | PDGFRA |
| chr4 | 54727443 | G | PDGFRA |
| chr5 | 1295184 | G | TERT |
| chr5 | 1295192 | G | TERT |
| chr6 | 152098823 | C | ERSR1 |
| chr7 | 140753310 | G | BRAF |
| chr7 | 55174013 | G | EGFR |
| chr7 | 55174016 | C | EGFR |
| chr7 | 55174021 | G | EGFR |
| chr7 | 55174025 | G | EGFR |
| chr7 | 55174048 | G | EGFR |
| chr7 | 55174049 | G | EGFR |
| chr7 | 55174765 | C | EGFR |
| chr7 | 55174769 | C | EGFR |
| chr7 | 55181349 | C | EGFR |
| chr7 | 55181355 | C | EGFR |
| chr7 | 55181361 | C | EGFR |
| chr7 | 55181364 | C | EGFR |
| chr7 | 55181371 | C | EGFR |
| chr7 | 55181382 | G | EGFR |
| chr7 | 55191810 | G | EGFR |
| chr7 | 55191856 | C | EGFR |
| chr9 | 136504900 | G | NOTCH1 |
| chr9 | 21971077 | C | CDKN2A |
| chr10 | 87933135 | G | PTEN |
| chr10 | 87933139 | G | PTEN |
| chr10 | 87933144 | G | PTEN |
| chr10 | 87933147 | C | PTEN |
| chr10 | 87933148 | G | PTEN |
| chr12 | 132676624 | C | POLE |

TABLE 4-continued

| Chromosome | Genomic Location (Hg38) | Base | Gene |
|---|---|---|---|
| chr12 | 68828834 | C | MDM2 |
| chr12 | 68828841 | C | MDM2 |
| chr13 | 32332602 | C | BRCA2 |
| chr14 | 104780182 | G | AKT1 |
| chr14 | 104780194 | C | AKT1 |
| chr14 | 104780230 | G | AKT1 |
| chr14 | 104780233 | G | AKT1 |
| chr15 | 66436832 | C | MAP2K1 |
| chr15 | 66436838 | C | MAP2K1 |
| chr15 | 66436841 | C | MAP2K1 |
| chr15 | 66436853 | C | MAP2K1 |
| chr17 | 39531209 | G | CDK12 |
| chr17 | 39531210 | G | CDK12 |
| chr17 | 39531225 | G | CDK12 |
| chr17 | 7673775 | C | TP53 |
| chr17 | 7673804 | C | TP53 |
| chr17 | 7673836 | C | TP53 |
| chr17 | 7674201 | G | TP53 |
| chr17 | 7674204 | G | TP53 |
| chr17 | 7675067 | C | TP53 |
| chr17 | 7675071 | G | TP53 |
| chr19 | 11021799 | C | SMARCA4 |
| chr19 | 11021822 | G | SMARCA4 |
| chr19 | 11021838 | G | SMARCA4 |
| chr19 | 1223136 | G | STK11 |
| chr19 | 1223144 | C | STK11 |
| chr19 | 1223165 | G | STK11 |
| chrX | 77558831 | G | ATRX |

The association of increased quantity of specific, individual 5hmC at or near specific Tier-1 hotspots in cancer cells provides a way to distinguish cancer cells from normal cells directly at specific base (C or G) resolution. Because 5hmC is not detected by normal sequencing technique as mutated, the increased 5hmC occurrence at specific hotspots is a more sensitive marker of cancerous cells before the occurrence of many mutations (e.g., C to T changes). Furthermore, the detection of these specifically selected, individual Tier-1 5hmC sites at or near hotspot CpG sites in cancer cell can be a more convenient, more direct cancer detection method than analysing the group 5hmC profile at chromosomal level or from hundreds of sequences of entire genes.

Thus, the detection and quantification of the number of selected specific individually targeted Tier-1 5hmC sites or its prevalence at or near many cancer mutation hot spots in a given cell enables one to detect, screen and predict the likelihood of cancer occurrence or the severity of the cancer. Moreover, the existence of 5hmC at many hotspots in cancer cell lines suggests a previously unknown higher order mechanism underlying the development of cancer. Markers along the 5hmC-mediated mechanism or pathway in cancer development are not only better diagnostic targets than mutations at hotspots, but also potentially better therapeutic targets. Drugs directly or indirectly either prevent 5hmC from occurring, prevent 5hmC from being converted to uracil- or thymine-analog, or correct 5hmC back to regular cytosine may prevent or treat cancer.

In one aspect, the present disclosure provides a method which includes:

extracting genomic deoxyribonucleic acid (DNA) from locations at or near specific target cancer hotspots from a subject;

modifying specific Tier-1 5-hydroxymethylcytosine (5hmC) on the DNA to a modified specific Tier-1 5hmC;

detecting and identifying presence or absence of the modified specific Tier-1 5hmC;

quantifying the detected and identified modified specific Tier-1 5hmC; and providing a report comprising a score, wherein the score is indicative of the likelihood of a status, a degree, or a severity of the risk of cancer.

In one embodiment of this aspect, the specific Tier-1 5hmC can exist in cancer cell lines, in transformed and immortalized cells.

In particular, the present disclosure provides selected specific Tier-1 5-hydroxymethylcytosine (5hmC) at or near cancer mutation hot spots as targets for early cancer detection. Such methods provide for high sensitivity detection of one or more genetic variants.

In another embodiment, the method comprises quantifying the detected and identified specific Tier-1 5hmC at or near cancer mutation hot spots located at a specific set of oncogenes in which, when mutated, a cytosine (C) is mutated to thymine (T), or a Guanine (G) is mutated to Adenine (A) on the complementary strand after amplification.

A cancer mutation hot spot is any single nucleotide having substitution mutations reported in the literature that is associated with any cancer. The cancer mutation hotspot can also be expressed as a single base on genomic DNA that is frequently observed to have single nucleotide variant (SNV) or deletion.

In another embodiment, modifying specific Tier-1 5hmC on the DNA to a modified 5hmC includes treating genomic deoxyribonucleic acid (DNA) to convert 5hmC on the DNA to a modified 5hmC includes any technique to modify 5hmC into another derivative of a nitrogenous base, such as derivative of a cytosine (C) or a thymine (T), or any non-nitrogenous molecule which can be detected as a different base from the original 5hmC. The detected different base can be used to calculate the quantity of 5hmC at any specific nucleotide locations on human genome.

In another embodiment, treating genomic deoxyribonucleic acid (DNA) to convert specific Tier-1 5hmC on the DNA to a modified 5hmC includes a method that employs either chemical or enzymatic reaction processes or both to modify the 5hmC into another derivative of a nitrogenous base, such as derivative of a cytosine (C) or a thymine (T), or any non-nitrogenous molecule which can be detected as a different base from the original 5hmC.

In another embodiment, treating genomic deoxyribonucleic acid (DNA) to convert specific Tier-1 5hmC on the DNA to a modified 5hmC includes a method that employs either oxidation or reduction reaction processes or both to modify the 5hmC into another derivative of a nitrogenous base, such as derivative of a cytosine (C) or a thymine (T), or any non-nitrogenous molecule which can be detected as a different base from the original 5hmC (C). In preferred embodiments, the oxidation or reduction reaction processes can be either chemical or enzymatic reactions.

Preferably, the oxidising agent may be an organic or inorganic chemical compound. Suitable oxidising agents are well known in the art and include metal oxides, such as Potassium perruthenate (KRuO4), Manganese dioxide (MnO2), Potassium permanganate (KMnO4). Particularly useful oxidising agents are those that may be used in aqueous conditions. However, oxidising agents that are suitable for use in organic solvents may also be employed where practicable. In some embodiments, the oxidising agent may comprise a perruthenate anion (RuO). Suitable perruthenate oxidising agents include organic and inorganic perruthenate salts, such as potassium perruthenate (KRuO4) and other metal perruthenates; tetraalkylammonium perruthenates, such as tetrapropylammonium perruthenate (TPAP) and tetrabutylammonium perruthenate (TB AP); polymer-supported perruthenate (PSP) and tetraphenylphosphonium ruthenate.

Advantageously, the oxidising agent or the oxidising conditions may also preserve the DNA in a denatured state. Optionally, the polynucleotide (DNA) may be subjected to further, repeat oxidising steps.

Suitable reducing agents are well-known in the art and include Pic-borane, Pyridine borane, Sodium borohydride (NaBH4), Sodium cyanoborohydride (NaCNBH4) and Lithium borohydride (LiBH4). Particularly useful reducing agents are those that may be used in aqueous conditions, as such are most convenient for the handling of the polynucleotide (DNA). However, reducing agents that are suitable for use in organic solvents may also be employed where practicable.

In another embodiment, the method further includes any technique for one of more of capturing, sequestering and enriching DNA fragments of 1000 base pair or less from any human tissue or cells by any molecule, such as monoclonal or polyclonal antibodies, having specific affinity in binding to specific Tier-1 5hmC. The captured, sequestered, or enriched DNA can be then analyzed to calculate the quantity of a variable which is a function of the quantity of cancer-specific genetic features, which include but not limit the quantity of cancer mutation hotspots.

In another embodiment, the method employs a method to quantify the number of detected specific Tier-1 5hmC occurred at or near a specific hotspot or multiple of hot spots or one or more cytosine near the hotspot.

In another embodiment, the present disclosure comprises any anti-cancer therapeutic methods or agents targeting either the specific Tier-1 5hmC itself, biochemical steps of converting regular cytosine to 5hmC, conversion of the 5hmC to uracil- or thymine-analog, or the 5hmC-mediated pathway that leads to cancer development.

In another embodiment, the method comprises any reference material, including but not limited to primary standard, secondary standard, calibrator, quality control, validation sample, using any of the specific Tier-1 5hmC at hotspot and its nearby region as part of the reference DNA sequence composition for diagnosis of cancer via specific Tier-1 5hmC detection, and quantification.

In another embodiment, the method includes quantifying a variable which is a function of a quantity of specific Tier-1 5-hydroxymethylcytosine (5hmC) at any specific nucleotide location on a human genome; and thereby detecting, screening or predicting a likelihood of cancer occurrence in a subject.

In another embodiment, the method provides the diagnostic methods that comprises the following steps:

Step 1: Modification of specific Tier-1 5hmC at locations which are at or near the said cancer hotspots.

Genomic DNA from human tissue (including plasma) is pre-extracted from patient specimen. It is subjected to a treatment to convert 5hmC on the DNA to a different moiety, such as an uracil, that is recognizable to identify the location of the 5hmC.

Examples of modification methods comprise the following:

(1) DNA containing 5hmC or the cancer hotspots and its adjacent region is oxidized by potassium perruthenate ($KRuO_4$) or other salts of high oxidation state of transition metals such as potassium permanganate ($KMnO_4$), or other oxidizing agent, to produce an aldehyde, such as 5-formylcytosine (5fC). 5fC is then reduced by a reducing agent such as Pic-borane or Pyridine borane to produce an uracil derivative dihydrouracil (DHU). DHU is then recognized as thymine (T) in the subsequence replication or amplification reaction involving RNA and/or DNA polymerase and any DNA sequence identification method. Alternatively, cytosine (C)'s complementary base, guanine (G) is recognized as Adenine (A) after replication or amplification reaction involving RNA and/or DNA polymerase and any DNA sequence identification method.

(2) DNA containing 5hmC or the cancer hotspots and its adjacent region is oxidized by enzymes such as Ten-eleven translocation (TET)1, TET2, and TET3, or another oxidative enzyme modifying 5hmC. The product of the oxidation of 5hmC is 5fC and subsequently 5-carboxylcytosine (5caC). These products are then reduced by reduction agents such as bisulfite ($NaHSO_3$) and produce derivative of uracil which is subsequently recognized as thymine (T) in the subsequence replication or amplification reaction involving RNA and/or DNA polymerase. Alternatively, cytosine (C)'s complementary base, guanine (G) is recognized as Adenine (A) after replication or amplification reaction involving RNA and/or DNA polymerase and any DNA sequence identification method. In addition to replication or amplification, C-to-T change or G-to-A change at the hotspot can be recognized (and distinguished from other nucleotides) by other methods disclosed in (1).

(3) The chemicals or enzymes in oxidations and reductions in (1) and (2) can be optionally switched to achieve the same modifying result, i.e., either C is converted to T, or after replication, its complementary base G is converted to A.

(4) Different modifications using oxidation or reduction can be applied to regular cytosine base (C), 5-methylcytosine (5mC), and 5hmC separately in order to produce different products so that the three can be distinguished and identified in subsequent procedures. For example, bisulfite reaction can distinguish regular cytosine from 5mC and 5hmC by modifying the regular cytosine. Alternatively, TET can separate both 5mC and 5hmC from regular cytosine by modifying both 5mC and 5hmC. In a separate experiment, 5mC and 5hmC can be distinguished by protection of 5hmC specifically from oxidation and reduction by using β-glucose transferase to attach glucose to the hydroxyl group of 5hmC to create 5-glucosyl-hydroxylmethyl-cytosine (5-ghmC). The unprotected 5mC can be reduced to produce DHU while the same reaction is blocked on 5-ghmC.

(5) Alternatively, regular cytosine, 5mC and 5-ghmC can be distinguished by their susceptibility to restriction digestion by enzymes such as MspI and HpaI.

(6) Specific sequence guided or sequence dependent recognition or cutting of DNA in the vicinity of regular cytosine, 5mC and 5-ghmC at or near a cancer mutation hotspot is performed via techniques such as DNA- or RNA-guided gene editing (such as Crisper technology), homologous recombination, or transposition via transposon.

Step 2: Detection, identification or confirmation of the presence or absence of modified 5hmC at specific Tier-1 locations which are at or near the said cancer hotspots.

Example (1) The DNA region having the modified specific Tier-1 5hmC is replicated, amplified or copied by DNA or RNA polymerase, the modified bases (from Step 1) contribute to the identification of the 5hmC and its location by being recognized by the polymerase as a different deoxy-ribonucleotide such as thymine (T, for modified C) or adenine (A) on its complementary strand.

(2) The DNA region having the protected specific Tier-1 5hmC (such as 5-ghmC) is replicated, amplified or copied by DNA or RNA polymerase as regular cytosine, while regular cytosine and other cytosine derivative such as 5mC are recognized as a different deoxyribonucleotide such as thymine (T) or adenine (A) on its complementary strand.

(3) The detection methods of (1) and (2) comprise various processes of replication or amplification mediated by DNA or RNA polymerase. These methods comprise, Sanger Sequencing, massive paralleled sequencing or Next Generation Sequencing (NGS), any form of single-cell-sequencing, such as technologies from Polymerase Chain Reaction (PCR), Droplet Digital PCR (ddPCR), Quantitative PCPacific Biosciences, Oxford Nanopore Technology, Quantapore (CA-USA), and Stratos (WA-USA), R (qPCR), Reverse Transcription PCR, isothermal amplification.

As examples shown in FIGS. 1A-1C, 2A-2D, 3 and 4 and Table 2 and 3, number of reads of 5hmC was obtained by NGS, and allele frequency (AF) can be calculated reflecting the frequency or amount of the detected 5hmC. The detection signal of Tier-1 5hmC can be generated by a single 5hmC site or multiple specific Tier-1 5hmC sites.

(4) The detection methods of (1) and (2) can include RNA-guided gene editing methods.

(5) Regular C, 5mC, 5hmC and their modified forms generated in Step 1 can be distinguished from each other by using different restriction enzymes that exhibit differential cutting efficiency among modified or unmodified forms. With or without PCR amplification, the size pattern of the restriction product can be compared using agarose gel or any form of chromatography.

(6) The detection methods of (1) and (2) can employ any technique to capture, sequester or enrich DNA fragments of 1000 base pair or less from any human tissue or cells by any molecule, such as monoclonal or polyclonal antibodies from any species, having specific and affinity in binding to 5hmC.

(7) In addition to replication or amplification, C-to-T change or G-to-A change at the hotspot can be recognized and distinguished from other nucleotides by other methods comprise chromatographical methods (e.g., size exclusion, affinity binding, ion-exchange chromatography), mass spectrometry, affinity binding and labelling methods utilizing antigen-antibody interaction (such as in ELISA), and molecule-to-molecule affinity binding (such as ligand-receptor binding).

Another example of detection method:

1) DNA oligos (primers) containing DNA sequence at or adjacent to Tier 1 sites were synthesized. These probes can be either immobilized on solid surface (flat or non-flat such as a magnetic bead surface) or chemically cross-linked to a moiety that is able to bind to a solid surface via affinity binding.

2) Labeled DNA oligos (probes) containing DNA sequence including one or multiple Tier 1 sites and sequences adjacent to them are synthesized. The deoxyribonucleotide at the Tier 1 5hmC location is a T (or A for the base complementary to 5hmC). This allows the probe to specifically hybridize to modified 5hmC after it is modified to uracil and subsequently amplified as T. The probe can serve as reporter (marker) during subsequent detection step (6).

3) The liquid biopsy sample (either from plasma or other body fluid) consists of numerous cell free DNA (cfDNA) derived from genomic DNA from either normal or tumor cells. The total cfDNA can be extracted from the sample using a variety of methods.

4) After extraction, cfDNA is subject to 5hmC modification (described in Step 1).

5) The pre-synthesized primers (oligos) from 1) are subjected to contacting with the modified extracted cfDNA (from 3)) via mixing or incubation under specific conditions promoting denaturation of the double stranded DNA, followed by hybridization of single-stranded DNA molecules based on complementary pairing scheme (ie. A to T, C to G).

6) The hybridized DNA is pulled out from the mixture via affinity binding followed by washing. This step can be skipped if enough DNA containing Tier 1 sites is available for analysis. If there is insufficient Tier 1 collected, multiple rounds of steps 2) to 5) can be done to accumulate sufficient DNA containing Tier 1 sites.

7) The probe from 2) is mixed with the hybridized DNA from 5) in a qPCR or ddPCR reaction. The labeled moiety of the probe provides signal indicating the quantity of the Tier 1 5hmC in the sample.

Figure 5:
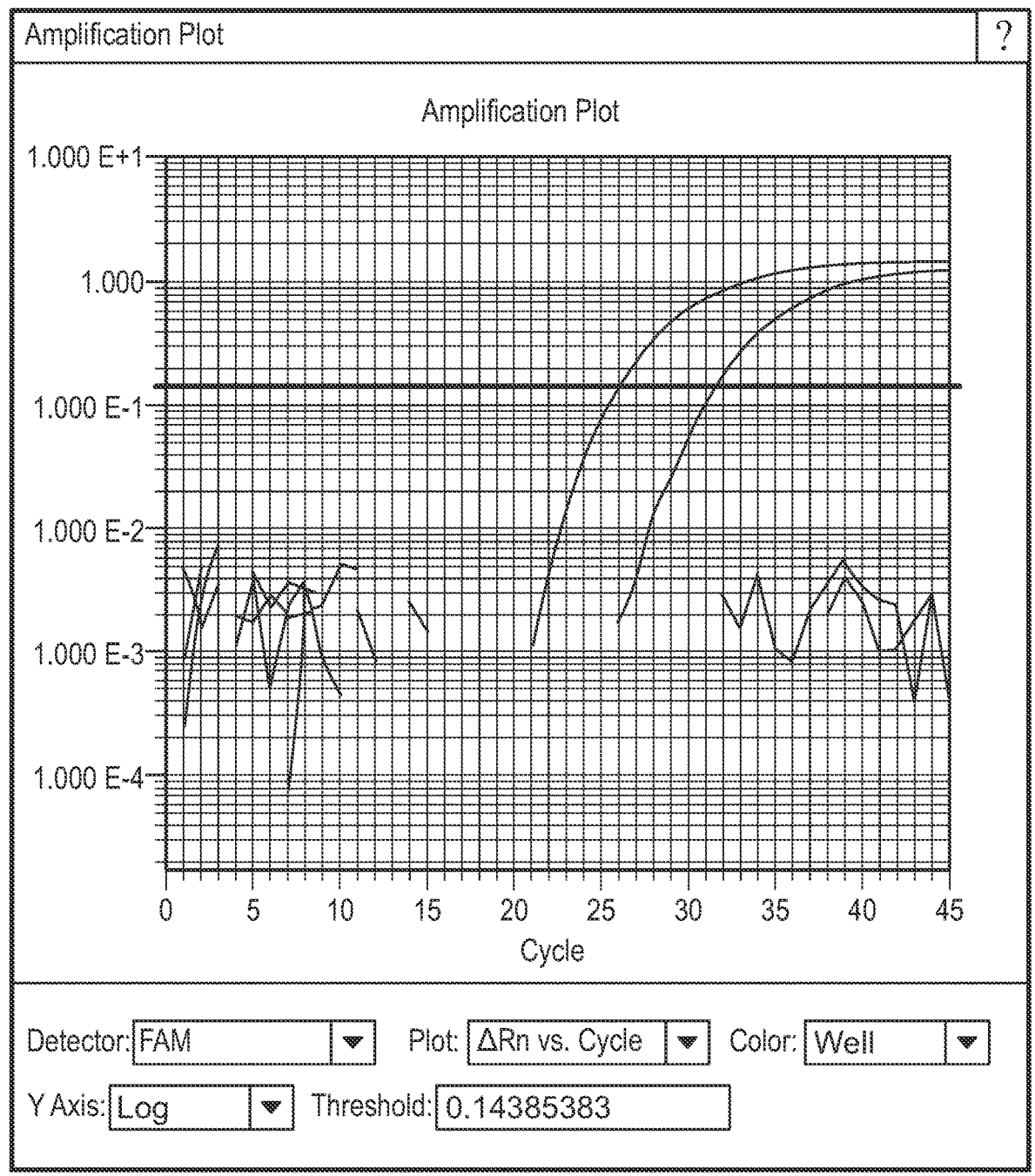
FIG. 5 illustrates an example amplification plot from qPCR.

8) FIG. 5 shows an example amplification plot from qPCR. Nine Tier-1 5hmC targets were selected from Table 4 for preparing the assay with primer and probes synthesized. Equal amount of gDNA from a pool of colorectal cancer patient and their matched normal colorectal tissue were extracted. Real-time florescence curves, indicating the real-time detection of 5hmC, were plotted. Cycle Threshold (Ct) values (26.1 for cancer sample and 31.6 for normal sample), which reflecting the relative concentration of the 5hmC, can be obtained.

Step 3: Quantification of the detected and identified 5hmC at locations which are at or near the said cancer hotspots.

Quantifying or recording the quantity of the occurrence of 5hmC can be of the following forms:

(1) Absolute number, count, read, or event of such 5hmC found in a given sample preparation.

(2) Absolute number, count, read, or event of such 5hmC detected on one or more specific genes in any given sample preparation. The quantified number can be either from a single specific Tier-1 5hmC or multiple Tier-1 5hmCs.

(3) Relative allele frequency or ratio or percentage of absolute numbers of 5hmC relative to either regular cytosine (C) or combination of regular C, 5mC and 5hmC at the same allele (base location) in situations in (1) and (2).

As examples shown in FIGS. 1A-1C and 2A-2D, 3 and 4, and Table 1 and 2, allele frequency (AF) was calculated indicating the quantification of the 5hmC based on the number of reads of 5hmC obtained by NGS.

(4) Relative numbers derived, transformed, or calculated from signal (e.g., florescence index), absorbance, intensity, color, hue, area of peak, or other measurements which reflect the numbers in (1), (2), or (3).

As an example in FIG. 5, difference in Ct values (DeltaCt) can be calculated to indicate the degree of 5hmC concentration difference. In addition, average, sum, square, exponential power, differences, ratio, or other simple mathematical operation or transformation that are used to reflect the quantity of the detected and identified specific Tier-1 5hmC at locations which are at or near the said cancer hotspots.

Step 4: The quantity of the quantitated number in Step 3 is applied to a predetermined algorithm so that a score is generated that is comparable to predetermined criteria that is indicative of the status, degree, severity, or size of the risk of cancer of that patient.

Examples (1) A score is a calculated value of a variable that is measuring of the propensity or likelihood of a patient's chance in getting cancer (or severity of cancer). In examples shown in FIG. 4, the score is a percentage calculated between AF of detected 5hmC in cfDNA versus gDNA from normal tissue.

(2) In example of FIG. 5, the score can either be the deltaCt or the deltaCt value can be converted into a ratio between concentrations of targeted Tier-1 5hmC in tumor and normal tissue. In this case, the ratio is 44.8.

The score calculated in (1) and (2) can be compared to a predetermined cut-off value (criteria or limit values, see Step 5) to determine the presence of tumor.

Step 5: Via mass observations (clinical trials) on a population of normal and pre-cancer or cancer patient samples, steps 1, 2 and 3 are used to generate raw data for generating an algorithm.

(1) The algorithm is a mathematical relationship between the quantified specific Tier-1 5hmC values (obtained in Step 3) and a score representing the degree of likelihood of having cancer.

(2) The score representing the likelihood of cancer can be obtained by giving a severity number to each patient based on the patient's size of tumor or stages of cancer.

(3) Regression models may be established between the quantified specific Tier-1 5hmC values (obtained in Step 3) and the score representing the likelihood of cancer.

(4) Based on large population of data, the cut-off value, the score that can separate normal or cancer patient can be statistically determined.

In another embodiment, the present disclosure provides both the Tier1 and Tier2 5hmC sites as targets for making contrived patient-like reference materials, including positive or negative quality control samples, standards (eg. a primary standard, a secondary standard, or a calibrator), or validation samples for assays aiming for detecting Tier1 or Tier2 5hmC to detect cancer. Synthetic DNA fragments mimicking the 5hmC patterns (at Tier1 or Tier2 sites) in genomic DNAs from either tumor cells or normal cells can be produced either through DNA synthesis in vitro or site-directed gene-editing in vivo. The resulting contrived sample can be used to monitoring the performance of the assay or calibrating the measurement system within the assay.

In another embodiment, the present disclosure provides anti-cancer therapeutic methods targeting Tier-1 5hmC at or near hotspot that comprises the following strategies:

(1) Methods or agents preventing the conversion from regular cytosine to 5hmC at or near cancer mutation hotspots.

Many biochemistry processes or pathways exist that result in 5hmCs, specifically located at or near cancer mutation hotspot, from regular cytosine or an intermediate, such as 5mC.

For example, enzymes Ten-eleven translocation (TET)1, TET2, and TET3 catalyzes the conversion of 5mC to 5hmC. Inhibitors of TET can be used to prevent this process. Specifically, any inhibitors that directly or indirectly inhibits the 5hmC formation at or near cancer mutation hotspot to achieve anti-cancer effect are encompassed within the scope of this disclosure.

Alternatively, methods or agents that prevent the formation of 5hmC at or near cancer hotspots through TET-independent mechanisms are also encompassed within the scope of this disclosure.

(2) Methods or agents preventing the formation of uracil- or thymine-analog from 5hmC at or near cancer mutation hotspots.

Any methods or agents that directly or indirectly inhibit the cellular process converting 5hmC to uracil- or thymine-analog at or near cancer mutation hotspots are encompassed within the scope of this disclosure.

(3) Methods or agents converting, directly or indirectly 5hmC to cytosine or another cytosine derivative (recognized as "C" by RNA or DNA polymerases) at or near cancer mutation hotspot are also encompassed within the scope of this disclosure.

All combinations of modification strategies, aimed to identify 5-hmC at locations which are at or near the said cancer hotspots are encompassed within the scope of this disclosure.

The above disclosure of this invention is directed primarily to embodiments and practices thereof. It will be readily apparent to those skilled in the art that further changes and modifications in actual implementation of the concepts described herein can easily be made or may be learned by practice of the invention, without departing from the spirit and scope of the invention as defined by the following claims.

We claim:

1. A method for determining the likelihood that a patient has or will develop cancer comprising:
   extracting genomic deoxyribonucleic acid (DNA) from locations at or near cancer hotspots from a human, wherein the at or near region of the cancer hotspot includes DNA with sequence 40 base pair upstream and 40 base pair downstream of the hotspot;
   modifying specific Tier-1 5-hydroxymethylcytosine (5hmC) on the DNA to a modified specific Tier-1 5hmC, wherein the specific Tier 1 5hmC are cytosine (C) residues that exhibit 3 to 8-fold likelihood of becoming 5hmCs in genomic DNAs from tumour cells than from normal cells at the same corresponding cytosine residue, and wherein modifying 5hmC comprises modifying 5hmC into a derivative of a nitrogenous base or a non-nitrogenous base which is a different base from unmodified 5hmC;
   detecting and identifying presence of the modified specific Tier-1 5hmC, wherein detecting and identifying comprises replicating, amplifying, or copying the DNA region having the modified specific Tier-1 5hmC by DNA or RNA polymerase;
   quantifying the detected and identified modified specific Tier-1 5hmC; and
   providing a report comprising a score, wherein the score is indicative of the likelihood of a status, a degree, or a severity of the risk of cancer, wherein the specific Tier-1 exist in cancer cell lines, in transformed and immortalized cells.

2. The method according to claim 1, wherein extracting genomic deoxyribonucleic acid (DNA) comprises pre-extracting the genomic deoxyribonucleic acid (DNA) from a tissue or plasma of the human.

3. The method according to claim 1, wherein the specific Tier-1 sites exist in cancerous cells in organs of the human.

4. The method according to claim 1, wherein the specific Tier-1 sites exist in colon of the human.

5. The method according to claim 1, wherein the modifying 5hmC comprises modifying 5hmC with chemical reactions, and wherein the chemical reactions comprise oxidation or reduction reaction.

6. The method according to claim 1, wherein the modifying 5hmC comprises modifying 5hmC with enzymatic reactions.

7. The method according to claim 1, wherein the modifying 5hmC comprises modifying 5hmC with an oxidation agent or a reduction agent.

8. The method according to claim 7, wherein the oxidation agent is selected from the group consisting of potassium perruthenate ($KRuO_4$), manganese dioxide ($MnO_2$), potassium permanganate ($KMnO_4$), tetrapropylammonium perruthenate (TPAP), tetrabutylammonium perruthenate (TBAP), polymer-supported perruthenate (PSP), tetraphenylphosphonium ruthenate, or a combination thereof.

9. The method according to claim 7, wherein the reduction agent is selected from the group consisting of pic-borane, pyridine borane, sodium borohydride ($NaBH_4$), sodium cyanoborohydride ($NaCNBH_4$), lithium borohydride ($LiBH_4$), or a combination thereof.

10. The method according to claim 1, wherein detecting and identifying comprises replicating, amplifying, or copying the DNA region having the modified specific Tier-1 5hmC by DNA or RNA polymerase.

11. The method according to claim 10, wherein detecting and identifying further comprises identifying the 5hmC and its location recognized by the DNA or RNA polymerase as a different deoxy ribonucleotide on its complementary strand.

12. The method according to claim 11, wherein the different deoxy ribonucleotide is cytosine (C) mutated to thymine (T), or a Guanine (G) mutated to Adenine (A) on the complementary strand.

13. The method according to claim 1, wherein quantifying the detected and identified modified specific Tier-1 5hmC comprises one or more of quantifying or recording the quantity of the occurrence of 5hmC.

14. The method according to claim 1, wherein the method further comprises using a reference material, wherein the reference material is selected from the group consisting of a primary standard, a secondary standard, a calibrator, a quality control, a validation sample.

15. The method according to claim 1, wherein the method comprises using the reference material for the specific Tier-1 5hmC at cancer hotspots and nearby region as a part of the reference DNA sequence composition for detection, and quantification.

* * * * *